United States Patent
Woo et al.

(10) Patent No.: US 10,487,158 B2
(45) Date of Patent: Nov. 26, 2019

(54) POLYPROPYLENE-BASED COMPOSITE MATERIAL

(71) Applicant: LG Chem, Ltd., Seoul (KR)

(72) Inventors: Ji Yoon Woo, Daejeon (KR); Hae Woong Park, Daejeon (KR); Choong Hoon Lee, Daejeon (KR); Hyo Ju Kim, Daejeon (KR); Sang Eun Park, Daejeon (KR); Young Woo Lee, Daejeon (KR); Ik Je Choe, Daejeon (KR)

(73) Assignee: LG Chem, Ltd. (KR)

( * ) Notice: Subject to any disclaimer, the term of this patent is extended or adjusted under 35 U.S.C. 154(b) by 122 days.

(21) Appl. No.: 15/749,323

(22) PCT Filed: Dec. 8, 2016

(86) PCT No.: PCT/KR2016/014361
§ 371 (c)(1),
(2) Date: Jan. 31, 2018

(87) PCT Pub. No.: WO2017/099486
PCT Pub. Date: Jun. 15, 2017

(65) Prior Publication Data
US 2018/0223014 A1 Aug. 9, 2018

(30) Foreign Application Priority Data

Dec. 8, 2015 (KR) .................. 10-2015-0174231
Oct. 5, 2016 (KR) .................. 10-2016-0128580

(51) Int. Cl.
| | |
|---|---|
| C08F 10/06 | (2006.01) |
| C08F 210/16 | (2006.01) |
| C08L 23/00 | (2006.01) |
| C08L 23/12 | (2006.01) |
| C08L 23/14 | (2006.01) |
| G01N 25/48 | (2006.01) |

(52) U.S. Cl.
CPC ............ C08F 10/06 (2013.01); C08F 210/16 (2013.01); C08L 23/00 (2013.01); C08L 23/12 (2013.01); C08L 23/14 (2013.01); *C08F 2500/01* (2013.01); *C08F 2500/03* (2013.01); *C08F 2500/08* (2013.01); *C08F 2500/12* (2013.01); *C08K 2201/003* (2013.01); *C08L 2207/02* (2013.01); *G01N 25/4866* (2013.01)

(58) Field of Classification Search
CPC .................. C08L 23/12; C08L 23/14
See application file for complete search history.

(56) References Cited

U.S. PATENT DOCUMENTS

| | | | |
|---|---|---|---|
| 5,064,802 | A | 11/1991 | Stevens et al. |
| 6,548,686 | B2 | 4/2003 | Nabika et al. |
| 7,355,089 | B2 | 4/2008 | Chang et al. |
| 2004/0087751 | A1 | 5/2004 | Tau et al. |
| 2004/0204547 | A1 | 10/2004 | Dharmarajan et al. |
| 2009/0105374 | A1* | 4/2009 | Wu .................. C08L 23/06 524/8 |
| 2010/0152390 | A1 | 6/2010 | De Gracia et al. |
| 2015/0094435 | A1 | 4/2015 | Cho et al. |

FOREIGN PATENT DOCUMENTS

| | | |
|---|---|---|
| KR | 2007-0121677 A | 12/2007 |
| KR | 2015-0034655 A | 4/2015 |
| WO | 2009042602 A1 | 4/2009 |

OTHER PUBLICATIONS

Extended European Search Report including Written Opinion for EP168733517 dated Aug. 21, 2018.
International Search Report From PCT/KR2016/014361 dated Mar. 17, 2017.

* cited by examiner

*Primary Examiner* — Wenwen Cai
(74) *Attorney, Agent, or Firm* — Lerner, David, Littenberg, Krumholz & Mentlik, LLP

(57) ABSTRACT

The present invention provides a polypropylene-based composite material capable of exhibiting excellent strength properties and impact strength properties, particularly, markedly improved impact strength properties at a low temperature without using a separate additive by including (A) polypropylene, and (B) an olefin-based polymer which satisfies the conditions of the following (b1) to (b4): (b1) density (d): from 0.850 to 0.910 g/cc, (b2) melt index (MI, 190° C., 2.16 kg load conditions): from 0.1 g/10 min to 100 g/10 min, (b3) molecular weight distribution (MWD): from 1.5 to 3.0, and (b4) i) two peaks are shown in a temperature range of −20° C. to 120° C. when taking measurements of temperature rising elution fractionation, and ii) a relation of $T(90)-T(50) \geq 60°$ C. is satisfied (where T(90) is a temperature at which 90 wt % of the olefin-based polymer is eluted, and T(50) is a temperature at which 50 wt % of the olefin-based polymer is eluted).

18 Claims, 11 Drawing Sheets

POLYPROPYLENE-BASED COMPOSITE MATERIAL

CROSS-REFERENCE TO RELATED APPLICATIONS

This application is a national phase entry under 35 U.S.C. § 371 of International Application No. PCT/KR2016/014361, filed Dec. 8, 2016, which claims priority to Korean Patent Application Nos. 10-2015-0174231, filed Dec. 8, 2015, and 10-2016-0128580, filed Oct. 5, 2016, the disclosures of which are incorporated herein by reference.

TECHNICAL FIELD

The present invention relates to a propylene-based composite material which is capable of showing excellent mechanical strength and remarkably improved impact strength at a low temperature.

Background Art

Generally, polypropylene-based resin compositions including polypropylene (PP) as a main component with an impact reinforcing agent and an inorganic filler have been used as compositions for parts of automotive interior or exterior materials.

By the mid-1990s, before developing ethylene-α-olefin copolymers which were polymerized by applying a metallocene catalyst, polypropylene-based resin compositions with ethylene propylene rubbers (EPR) or ethylene propylene diene rubbers (EPDM) as an impact reinforcing agent have been widely used as automotive interior or exterior materials, particularly, materials for a bumper cover. However, since the appearance of ethylene-α-olefin copolymers which were synthesized using a metallocene catalyst, the ethylene-α-olefin copolymers were put into use as impact reinforcing agents and now are mainstreams. This is because polypropylene-based composite materials using thereof have balanced physical properties such as impact strength, elasticity and bending strength, and various merits including good moldability and low costs.

The molecular structure of polyolefins such as ethylene-α-olefin copolymers which are synthesized using a metallocene catalyst is controlled uniformly when compared to that synthesized using a Ziegler-Natta catalyst, and rather has narrow molecular weight distribution and excellent mechanical properties. Ethylene elastomers with a low density, which are synthesized using a metallocene catalyst, are relatively uniformly inserted into polyethylene (PE) molecules when compared to that synthesized using α-olefin copolymer monomers by a Ziegler-Natta catalyst, and rubber properties with a low density are maintained and excellent other mechanical properties are attained.

However, the securing of impact resistance is limited according to diverse service environments, and the development of polypropylene-based composite materials which may overcome such limitations is required.

DISCLOSURE OF THE INVENTION

Technical Problem

An aspect of the present invention for solving is to provide a polypropylene-based composite material which is capable of showing excellent mechanical strength and remarkably improved impact strength properties at a low temperature.

In addition, another aspect of the present invention for solving is to provide a molded article and a part of an automobile, which are manufactured using the polypropylene-based composite material.

Technical Solution

According to an embodiment of the present invention, there is provided a polypropylene-based composite material including (A) polypropylene; and (B) an olefin-based polymer satisfying the following conditions of (b1) to (b4):

(b1) density (d): from 0.850 g/cc to 0.910 g/cc, (b2) melt index (MI, 190° C., 2.16 kg load conditions): from 0.1 g/10 min to 100 g/10 min, (b3) molecular weight distribution (MWD): from 1.5 to 3.0, and (b4) i) two peaks are shown in a temperature range of −20° C. to 120° C. when taking measurements of temperature rising elution fractionation (TREF), and ii) a relation of T(90)−T(50)≥60° C. is satisfied (where T(90) is a temperature at which 90 wt % of the olefin-based polymer is eluted, and T(50) is a temperature at which 50 wt % of the olefin-based polymer is eluted).

According to another embodiment of the present invention, there is provided a polypropylene-based composite material including (A2) at least one random propylene copolymer having a melting point in a range of 120° C. to 160° C. when taking measurements of differential scanning calorimetry (DSC) (hereinafter, will be referred to as "DSC melting point"), and a melt flow rate in a range of 5 g/10 min to 120 g/10 min, in an amount of 75 wt % to 97 wt %; and (B2) an ethylene a-olefin copolymer satisfying the conditions of the following (b21) to (b25), in an amount of 3 wt % to 25 wt %:

(b21) density: from 0.860 g/cc to 0.910 g/cc, (b22) melt index (190° C., 2.16 kg load conditions): from 0.1 g/10 min to 200 g/10 min, (b23) molecular weight distribution: from 1.5 to 3.0, (b24) i) two peaks are shown in a temperature range of −20° C. to 120° C. when taking measurements of temperature rising elution fractionation, and ii) a relation of T(90)−T(50)≥60° C. is satisfied (where T(90) is a temperature at which 90 wt % of the olefin-based polymer is eluted, and T(50) is a temperature at which 50 wt % of the olefin-based polymer is eluted), and (b25) weight average molecular weight: from 10,000 g/mol to 500,000 g/mol.

According to further another embodiment of the present invention, there are provided a molded article and a part of an automobile, which are manufactured using the polypropylene-based composite material.

Advantageous Effects

The polypropylene composite material according to the present invention may show excellent mechanical strength and markedly improved impact strength properties at a low temperature without using a separate additive by including an olefin-based polymer which exhibits excellent impact strength improving effects by controlling crystallinity, and excellent miscibility with polypropylene and thus may be uniformly dispersed in a composite material. As a result, the polypropylene-based composite material may be used in diverse fields including an automobile, a wire, a toy, a fiber, a medicine, or the like, particularly, for a part of an automobile which requires particularly high impact strength.

BRIEF DESCRIPTION OF THE DRAWINGS

The accompanying drawings in the present disclosure illustrate preferred embodiments of the present invention and are included together with the above description to provide a further understanding of the inventive concept. The inventive concept, however, should not be construed as limited to the accompanying drawings.

BEST MODE FOR CARRYING OUT THE INVENTION

Figure 1:
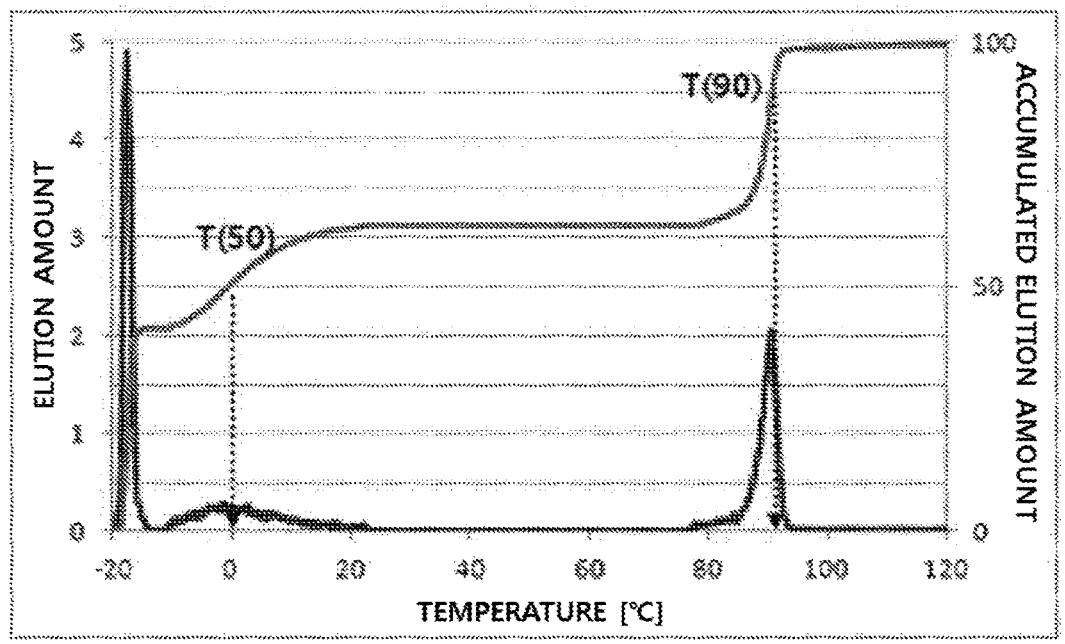
FIG. 1 illustrates a temperature rising elution fractionation (TREF) graph of an olefin-based polymer prepared in Preparation Example 1.

Hereinafter, the present invention will be described in more detail to assist the understanding of the present invention.

It will be understood that terms or words used in the specification and claims, should not be interpreted as having a meaning that is defined in dictionaries, but should be interpreted as having a meaning that is consistent with their meaning in the context of the present invention on the basis of the principle that the concept of the terms may be appropriately defined by the inventors for the best explanation of the invention.

In the present disclosure, the term "polymer" denotes a polymer compound prepared by the polymerization of monomers which have the same or different types. The general term of the "polymer" includes "hybrid polymer" as well as "homopolymer," "copolymer" and "tercopolymer". In addition, the "hybrid polymer" denotes a polymer prepared by the polymerization of at least two different types of monomers. The general term of the "hybrid polymer" denotes the "copolymer" which is commonly used for denoting a polymer prepared using two different types of monomers and the "tercopolymer" which is commonly used for denoting a polymer prepared using three different types of monomers. The "hybrid polymer" includes a polymer prepared by the polymerization of at least four different types of monomers.

Generally, polypropylene is used as interior or exterior materials of an automobile including a car bumper, and in order to correct the low impact strength of the polypropylene, a polyolefin-based polymer is used together as an impact reinforcing agent. Particularly, a polyolefin-based polymer with a low density is used to attain properties such as impact resistance, elasticity, and tensile properties according to various service environments, and high impact strength properties, but in this case, there is an issue of rather degrading the strength of the polypropylene.

In contrast, in the present invention, excellent mechanical strength and markedly improved impact strength properties at a low temperature may be attained without using a separate additive, by using a polyolefin-based polymer which shows excellent improving effects of impact strength and can be uniformly dispersed in a composite material due to excellent miscibility with polypropylene during a preparation of the polypropylene-based composite mate.

That is, the polypropylene-based composite material according to an embodiment of the present invention includes:

(A) polypropylene; and
(B) an olefin-based polymer satisfying the following conditions of (b1) to (b4):
(b1) density (d): from 0.850 g/cc to 0.910 g/cc,
(b2) melt index (MI, 190° C., 2.16 kg load conditions): from 0.1 g/10 min to 200 g/10 min, more particularly, from 0.1 g/10 min to 100 g/10 min, (b3) molecular weight distribution (MWD): from 1.5 to 3.0, and (b4) i) two peaks are shown in a temperature range of −20° C. to 120° C. when taking measurements of temperature rising elution fractionation (TREF), and ii) a relation of T(90)−T(50)≥60° C. is satisfied (where T(90) is a temperature at which 90 wt % of the olefin-based polymer is eluted, T(50) is a temperature at which 50 wt % of the olefin-based polymer is eluted, and the yield of a polymer may be calculated as the integral value of a temperature-elution amount graph in TREF).

Hereinafter, each constituent component will be explained in detail.

(A) Polypropylene

In the polypropylene composite material according to an embodiment of the present invention, the polypropylene may be a polypropylene homopolymer, or a copolymer of propylene and alpha-olefin monomer. In this case, the copolymer may be an alternating, random, or block copolymer. However, in the present invention, polypropylene which may be a duplication of the olefin polymer is excluded, and the polypropylene is a different compound from the olefin polymer.

The alpha-olefin-based monomer may be particularly an aliphatic olefin of 2 to 12 carbon atoms, or 2 to 8 carbon atoms. More particularly, any one of ethylene, propylene, 1-butene, 1-pentene, 3-methyl-1-butene, 1-hexene, 4-methyl-1-pentene, 3-methyl-1-pentene, 1-heptene, 1-octene, 1-decene, 1-undecene, 1-dodecene, 1-tetradecene, 1-hexadecene, 1-itocene, 4,4-dimethyl-1-pentene, 4,4-diethyl-1-hexene, 3,4-dimethyl-1-hexene, or the like, or a mixture of at least two thereof may be used.

More particularly, the polypropylene may be any one selected from the group consisting of a polypropylene copolymer, a propylene-alpha-olefin copolymer, and a propylene-ethylene-alpha-olefin copolymer, or a mixture of at least two thereof. In this case, the copolymer may be a random or block copolymer.

In addition, the polypropylene may have melt index (MI) of 0.5 g/10 min to 100 g/10 min, particularly, 1 g/10 min to 90 g/10 min, more particularly, 10 g/10 min to 50 g/10 min when taking measurements at 230° C. and 2.16 kg load. If the melt index of the polypropylene is out of the range, it is apprehended that defects may be generated during injection molding.

Particularly, in the polypropylene-based composite material according to an embodiment of the present invention, the polypropylene may be an impact copolymer of which melt index (MI) is 0.5 g/10 min to 100 g/10 min, particularly, 1 g/10 min to 90 g/10 min when taking measurements at 230° C. and 2.16 kg load, and more particularly, may be a propylene-ethylene impact copolymer. The impact copolymer may be included in an amount of 50 wt % to 90 wt %, more particularly, wt % 90 wt % based on the total amount of the polypropylene-based composite material. If the impact copolymer having such physical properties is included as the polypropylene in the above amount range, strength properties, particularly, strength properties at a low temperature may be enhanced.

The impact copolymer may be prepared to satisfy the physical property conditions by using a common polymer preparation reaction, or may be commercially purchased and used. Particular example may include SEETE™ M1600 of LG Chem. Ltd.

In addition, in the polypropylene composite material according to an embodiment of the present invention, the polypropylene may be at least one random propylene copolymer having a DSC melting point in a range of 120° C. to 160° C., and melt flow rate (MFR) in a range of 5 g/10 min to 120 g/10 min when taking measurements at 230° C. and 2.16 kg load conditions according to ASTM-D 1238. The random propylene copolymer may be included in an amount of 75 wt % to 97 wt %, more particularly, 85 wt % to 91 wt % based on the total amount of the polypropylene-based composite material. If the polypropylene having such physical properties is included in the amount range, the mechanical strength of the polypropylene composite material such as hardness may be increased. The random propylene copolymer may be prepared to satisfy the physical property conditions by using a common polymer preparation reaction or may be commercially purchased and used. Particular example may include Braskem™ PP R7021-50RNA of Braskem America Inc., or Formolene™ 7320A of Formosa Plastics Corporation.

(B) Olefin-based Polymer

Meanwhile, the olefin-based polymer included in the polypropylene-based composite material according to an embodiment of the present invention satisfies physical property conditions including density, melt index, molecular weight distribution, and elution temperature of (b1) to (b4) at the same time.

Particularly, the olefin-based polymer according to an embodiment of the present invention shows a low density of 0.850 to 0.910 g/cc when taking measurements according to ASTM D-792.

Generally, the density of an olefin-based polymer is influenced by the kinds and amounts of monomers used for polymerization, a polymerization degree, or the like, and in case of a copolymer, influence by the amount of a comonomer is significant. In the present invention, a large amount of comonomers may be introduced due to the use of a metallocene-based catalyst composition including different kinds of transition metal compounds having distinguishing structures. As a result, the olefin-based polymer according to an embodiment of the present invention has a low density in the above-described range, and as a result, may exhibit excellent impact strength. More particularly, the olefin-based polymer may have a density of 0.860 to 0.910 g/cc, more particularly, 0.860 g/cc to 0.890 g/cc, and in this case, the maintenance of mechanical properties and the improving effect of impact strength according to the control of density are even more remarkable.

In addition, the mechanical properties and impact strength of an olefin-based polymer, and melt index (MI) which influences moldability may be controlled by adjusting the amount used of a catalyst during a polymerization process. The olefin-based polymer according to an embodiment of the present invention may show melt index (MI) of particularly 0.1 to 200 g/10 min, more particularly, 0.1 to 100 g/10 min when taking measurements according to ASTM D1238 at 190° C. under load conditions of 2.16 kg in the above-described low density conditions, and may show excellent impact strength without degrading mechanical properties. In consideration of the remarkable improving effects with good balance of mechanical properties and impact strength, the olefin-based polymer may further more particularly have melt index of 0.1 g/10 min to 50 g/10 min.

In addition, if at least two kinds of polymers are mixed, molecular weight distribution (MWD) is generally increased, and as a result, impact strength and mechanical properties are decreased, and blocking phenomenon or the like arises. The olefin-based polymer according to an embodiment of the present invention uses a metallocene-based catalyst composition including different kinds of transition metal compounds having distinguishing structures, and a single peak, that is, a monomodal-type peak is shown in a molecular weight distribution curve when taking measurements of GPC even though at least two kinds of polymers are mixed. In addition, the olefin-based polymer according to an embodiment of the present invention shows narrow molecular weight distribution, and as a result, may show excellent impact strength. Particularly, the olefin-based polymer may have molecular weight distribution (MWD) of 1.5 to 3.0, more particularly, 1.5 to 2.8, which is the ratio (Mw/Mn) of a weight average molecular weight (Mw) and a number average molecular weight (Mn).

In addition, the olefin-based polymer may have a weight average molecular weight (Mw) of 10,000 g/mol to 500,000 g/mol, particularly, 20,000 g/mol to 200,000 g/mol, more particularly, 50,000 g/mol to 150,000 g/mol, further more particularly, 50,000 g/mol to 100,000 g/mol in the molecular weight distribution range.

in the present invention, the weight average molecular weight (Mw) and the number average molecular weight (Mn) are a polystyrene conversion molecular weight which is analyzed by gel permeation chromatography (GPC).

The physical properties of an olefin-based polymer which is polymerized using a common metallocene catalyst are determined during compounding according to the crystallinity thereof, and generally, the olefin-based polymer has single crystallinity showing one peak in a temperature range of $-20°$ C. to $120°$ C. when taking measurements of TREF, and T(90)–T(50) of $10°$ C. to $30°$ C. In contrast, the olefin-based polymer according to an embodiment of the present invention includes different kinds of crystal structures which have a large crystallinity difference, and may show improved impact strength and improved mechanical properties at the same time during compounding.

Particularly, the olefin-based polymer according to an embodiment of the present invention has, when taking measurements of temperature rising elution fractionation (TREF), i) two peaks in a temperature range of $-20°$ C. to $120°$ C. and ii) T(90)–T(50), which is the difference between T(50) which is an elution temperature at which 50 wt % of the olefin-based polymer is eluted and T(90) which is an elution temperature at which 90 wt % of the olefin-based polymer is eluted, of $60°$ C. or more, particularly, $70°$ C. or more, more particularly, from $70°$ C. to $110°$ C., further more particularly, from $80°$ C. to $110°$ C.

Generally, if two or more kinds of olefin-based polymers with different density and crystallinity are respectively prepared in separate reactors, and then blended, two peaks may be shown when taking measurements of TREF of the composition thus mixed or the olefin block copolymer thereof. On the other hand, in the present invention, crystallinity distribution is controlled widely by a continuous solution polymerization in a single reactor, and two peaks are shown when taking measurements of TREF in a state where a block is not formed in a polymer, and T(90)–T(50) is $60°$ C. or more, particularly, $70°$ C. or more, more particularly, from $70°$ C. to $110°$ C., further more particularly, from $80°$ C. to $110°$ C., resulting a very large difference.

In addition, two peaks may be shown on TREF not in an olefin-based polymer but in a linear low-density ethylene-based polymer to which a Ziegler-Matta catalyst system is applied, but a relation of T(90)–T(50)<$50°$ C. is attained, thereby resulting in a small difference.

In addition, the olefin-based polymer according to an embodiment of the present invention may have two peaks in a temperature range of $-20°$ C. to $120°$ C. and T(90) of $70°$ C. or more (T(90)≥$70°$ C.), particularly, $80°$ C. or more, more particularly, $85°$ C. to $120°$ C. when taking measurements of TREF due to a crystal structure with high crystallinity, which serves mechanical strength. Meanwhile, in an olefin-based polymer which is polymerized using a common metallocene catalyst, T(90) is shown in a measurement range of $-20°$ C. to $120°$ C. according to the density and crystallinity thereof, and is difficult to delimit.

In the present invention, TREF may be measured by using a TREF machine of PolymerChar Co. and particularly, may be measured while elevating the temperature from $-20°$ C. to $120°$ C. using o-dichlorobenzene as a solvent.

In addition, in the present invention, T(50) means the temperature at a point where the elution of 50 wt % of the total elution amount is terminated in a TREF elution graph expressed by an elution amount with respect to temperature (dC/dT), and T(90) means the temperature at a point where the elution of 90 wt % of the total elution amount is terminated in a TREF elution graph expressed by an elution amount with respect to temperature (dC/dT). In addition, for calculating T(90) and T(50), the initiation point of each peak in the graph of elution amount with respect to temperature (dC/dT) may be defined as a point where the elution of a polymer is initiated based on a base line, and the end point of each peak may be defined as a point where the elution of a polymer is terminated based on a base line. In addition, a peak expressed in $-20°$ C. to $-10°$ C. may be regarded as a portion of a peak expressed in after $-10°$ C., which is shown in this position due to the limitation of measurement. Accordingly, the peak expressed in this position may be included and treated as a peak expressed in after $-10°$ C.

In addition, the olefin-based polymer according to an embodiment of the present invention may have an accumulated elution amount via purging of less than $-20°$ C., or in a temperature range of $-20°$ C. to $10°$ C. when taking measurements of temperature sing elution fractionation, of 20 wt % to 80 wt %, more particularly, 30 wt % to 80 wt %, further more particularly, 50 wt % to 70 wt % based on the total amount of a polymer.

The olefin-based polymer according to an embodiment of the present invention may particularly be a homopolymer of olefin-based monomers, for example, any one selected from the group consisting of an alpha-olefin-based monomer, a cyclic olefin-based monomer, a diene olefin-based monomer, a triene olefin-based monomer and a styrene-based monomer, or a copolymer of at least two thereof. More particularly, the olefin-based polymer may be a copolymer of ethylene with alpha-olefin of 3 to 12 carbon atoms or 3 to 8 carbon atoms, and further more particularly, may be a copolymer of ethylene with propylene, ethylene with 1-butene, ethylene with 1-hexene, ethylene with 4-methyl-1-pentene, or ethylene with 1-octene. In addition, if the olefin-based polymer is the copolymer of ethylene with alpha-olefin, the amount of the alpha-olefin may be 90 wt % or less, more particularly, 70 wt % or less, further more particularly, 5 to 50 wt % based on the total amount of the copolymer. Within the range, the above-described physical properties may be easily accomplished, excellent miscibility with polypropylene may be shown, and as a result, even more improved impact strength effects may be exhibited.

The olefin-based polymer according to an embodiment of the present invention, which has the above-described physical properties and constitutional characteristics may be prepared by a continuous solution polymerization reaction in the presence of a metallocene catalyst composition including at least one kind of a transition metal compound in a single reactor. Accordingly, in the olefin-based polymer according to an embodiment of the present invention, a block formed by linearly connecting two or more repeating units derived from one monomer among monomers constituting a polymer in the polymer is not formed. That is, the olefin-based polymer according to the present invention does not include a block copolymer, but may be selected from the group consisting of a random copolymer, an alternating copolymer and a graft copolymer, more particularly, may be a random copolymer.

Particularly, the olefin-based polymer may be prepared by a preparation method including a step of polymerizing an olefin-based monomer using a catalyst composition including a first transition metal compound of Formula and a second transition metal compound of Formula 2 in an weight ratio of 50:50 to 80:20. Accordingly, in another embodiment of the present invention, a preparation method of the olefin-based polymer is provided. However, in the preparation of an olefin-based polymer according to an embodiment of the present invention, the structure ranges of the first transition metal compound and the second transition metal compound are not limited to specifically disclosed types, but all modifications, equivalents, or replacements included in the scope and technical range of the present invention should be understood to be included in the present invention.

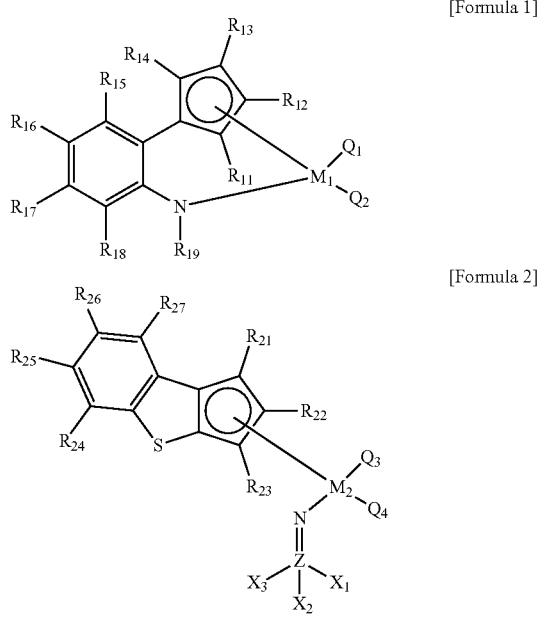

[Formula 1]

[Formula 2]

In Formulae 1 and 2, $M_1$ and $M_2$ are each independently a transition metal in group 4, $Q_1$, $Q_2$, $Q_3$, and $Q_4$ are each independently selected from the group consisting of a hydrogen atom, a halogen group, an alkyl group of 1 to 20 carbon atoms, an alkenyl group of 2 to 20 carbon atoms, a cycloalkyl group of 3 to 20 carbon atoms, an aryl group of 6 to 20 carbon atoms, an alkylaryl group of 6 to 20 carbon atoms, an arylalkyl group of 7 to 20 carbon atoms, an alkylamino group of 1 to 20 carbon atoms, an arylamino group of 6 to 20 carbon atoms, and an alkylidene group of 1 to 20 carbon atoms, $R_{11}$ to $R_{14}$ are each independently selected from the group consisting of a hydrogen atom, a halogen group, a silyl group, an alkyl group of 1 to 20 carbon atoms, an alkenyl group of 2 to 20 carbon atoms, a cycloalkyl group of 3 to 20 carbon atoms, an aryl group of 6 to 20 carbon atoms, an alkylaryl group of 7 to 20 carbon atoms, an arylalkyl group of 7 to 20 carbon atoms, and a metalloid radical of a metal in group 14 substituted with a hydrocarbyl group of 1 to 20 carbon atoms; or at least two adjacent functional groups of $R_{11}$ to $R_{14}$ are connected to each other to form an aliphatic ring of 5 to 20 carbon atoms or an aromatic ring group of 6 to 20 carbon atoms, which is unsubstituted or substituted with at least one substituent selected from the group consisting of a halogen group, an alkyl group of 1 to 20 carbon atoms, an alkenyl group of 2 to 20 carbon atoms, and an aryl group of 6 to 20 carbon atoms, $R_{15}$ to $R_{19}$ are each independently selected from the group consisting of a hydrogen atom, a halogen group, a silyl group, an alkyl group of 1 to 20 carbon atoms, an alkenyl group of 2 to 20 carbon atoms, a cycloalkyl group of 3 to 20 carbon atoms, an aryl group of 6 to 20 carbon atoms, an alkylaryl group of 7 to 20 carbon atoms, and an arylalkyl group of 7 to 20 carbon atoms, or at least two adjacent functional groups of $R_{15}$ to $R_{19}$ are connected to each other to form an aliphatic ring of 5 to 20 carbon atoms or an aromatic ring of 6 to 20 carbon atoms, wherein the aliphatic ring or the aromatic ring is unsubstituted or substituted with at least one substituent selected from the group consisting of a halogen group, an alkyl group of 1 to 20 carbon atoms, an alkenyl group of 2 to 20 carbon atoms, and an aryl group of 6 to 20 carbon atoms, $R_{21}$ to $R_{27}$ are each independently selected from the group consisting of a hydrogen atom, a halogen group, a hydrocarbyl group of 1 to 20 carbon atoms, a hetero hydrocarbyl group of 1 to 20 carbon atoms, and a metalloid radical of a metal in group 14 substituted with a hydrocarbyl group of 1 to 20 carbon atoms, and particularly, $R_{21}$ to $R_{27}$ are each independently selected from the group consisting of a hydrogen atom, a halogen group, a silyl group, an alkyl group of 1 to 20 carbon atoms, an alkenyl group of 2 to 20 carbon atoms, a cycloalkyl group of 3 to 20 carbon atoms, an aryl group of 6 to 20 carbon atoms, an alkylaryl group of 7 to 20 carbon atoms, an arylalkyl group of 7 to 20 carbon atoms, and a metalloid radical of a metal in group 14 substituted with a hydrocarbyl group of 1 to 20 carbon atoms;

$X_1$ to $X_3$ are each independently selected from the group consisting of a hydrogen atom, a halogen group, a hydrocarbyl group of 1 to 20 carbon atoms, and a hetero hydrocarbyl group of 1 to 20 carbon atoms, and more particularly are each independently selected from the group consisting of a hydrogen atom, a halogen group, a silyl group, an amino group, an (alkyl of 1 to 20 carbon atoms)amino group, an alkyl group of 1 to 20 carbon atoms, an alkenyl group of 2 to 20 carbon atoms, a cycloalkyl group of 3 to 20 carbon atoms, an aryl group of 6 to 20 carbon atoms, an alkylaryl group of 7 to 20 carbon atoms, and an arylalkyl group of 7 to 20 carbon atoms; or at least two adjacent functional groups of $X_1$ to $X_3$ are connected to each other to form an aliphatic ring of 5 to 20 carbon atoms or an aromatic ring of 6 to 20 carbon atoms, which is substituted with at least one substituent selected from the group consisting of a halogen group, a silyl group, an amino group, an (alkyl of 1 to 20 carbon atoms)amino group, an alkyl group of 1 to 20 carbon atoms, an alkenyl group of 2 to 20 carbon atoms, and an aryl group of 6 to 20 carbon atoms, and Z is phosphor (P), arsenic (As), or antimony (Sb).

In the transition metal compound of Formula 1, a metal site is connected to cyclopentadienyl ligand introducing an amino group which is connected to a phenylene bridge, and the structure thereof has a narrow Cp-$M_1$-N angle and a wide $Q_1$-$M_1$-$Q_2$ angle to which a monomer approaches. In addition, different from a CGC structure connected by a silicon bridge, the cyclopentadiene, the phenylene bridge, nitrogen and the metal ($M_1$) are connected in order via the bonding of a ring shape to form a stable and rigid pentagonal ring structure in the transition metal compound structure of Formula 1. That is, the nitrogen atom of an amino group is connected to the phenylene bridge via two bonds in a ring shape to attain a stronger complex structure. Thus, when such transition metal compounds are reacted with a cocatalyst such as methyl aluminoxane or $B(C_6F_5)_3$, activated, and applied to the polymerization of olefin, an olefin polymer having high activity and high copolymerization degree may be produced even at a high polymerization temperature. Particularly, since a large amount of alpha-olefin may be introduced as well as polyethylene having a low density due to a structural characteristic of a catalyst, a polyolefin copolymer having a low density of 0.910 g/cc or less, more particularly, a density of 0.850 to 0.910 g/cc degree may be produced. In addition, a polymer having narrow MWD with respect to CGC, good copolymerization degree and high molecular weight in a low density region may be prepared by using a catalyst composition including the transition metal compound.

In addition, diverse substituents may be introduced to a cyclopentadienyl ring and a quinoline-based ring in the structure of the transition metal compound of Formula 1, and ultimately, electronic and steric environment around a metal may be easily controlled, and so, the structure and physical properties of the polyolefin thus produced may be easily controlled. The transition metal compound of Formula 1 may be preferably used for preparing a catalyst for polymerizing olefin monomers. However, the present invention is not limited thereto, and the transition metal compound may be applied in all other fields which use thereof.

In addition, the transition metal compound of Formula 2 which is mixed and used with the transition metal compound of Formula 1 has a structure in which an imide-based ligand such as phosphinimide ligands is connected to cyclopentadiene derivatives having heterocycle including sulfur. Accordingly, if the transition metal compound of Formula 2 is used as a catalyst during the copolymerization of an olefin-based polymer of ethylene with octene, hexene, or butene, high catalyst activity is shown, and an olefin-based polymer having excellent physical properties such as a high molecular weight and a low density may be prepared. In addition, the miscibility of the transition metal compound of Formula 2 with the transition metal compound of Formula 1 is excellent, and the homogeneous mixing thereof in a catalyst composition may be attained, thereby further improving the catalyst activity of a catalyst composition.

Meanwhile, the alkyl group in the present disclosure means, if not specifically defined, linear and branched aliphatic saturated hydrocarbon groups of 1 to 20 carbon atoms. Particularly, the alkyl group includes a linear or branched alkyl group of 1 to 20 carbon atoms, more particularly, 1 to 6 carbon atoms. Particular examples of the alkyl group may include a methyl group, an ethyl group, an n-propyl group, an isopropyl group, an n-butyl group, an isobutyl group, a sec-butyl group, a t-butyl group, a pentyl group, an iso-amyl group, a hexyl group, or the like.

In addition, the alkoxy group in the present disclosure means, if not specifically defined, a linear or branched alkyl group of 1 to 20 carbon atoms, which is combined with oxygen (—OR). Particularly, the alkyl group may include an alkoxy group of 1 to 20 carbon atoms, more particularly, 1 to 6 carbon atoms. Particular examples of the alkoxy group may include a methoxy group, an ethoxy group, a propoxy group, a butoxy group, a t-butoxy group, or the like.

In addition, the alkenyl group in the present disclosure means, if not specifically defined, linear and branched aliphatic unsaturated hydrocarbon groups of 2 to 20 carbon atoms including a carbon-carbon double bond. Particularly, the alkenyl group includes an alkenyl group of 2 to 6 carbon atoms. Particular examples of the alkenyl group may include an ethenyl group, a propenyl group, a butenyl group, or the like.

In addition, the cycloalkyl group in the present disclosure means, if not specifically defined, a cyclic saturated hydrocarbon group of 3 to 20 carbon atoms. Particularly, the cycloalkyl group includes a cycloalkyl group of 3 to 6 carbon atoms. Particular examples of the cycloalkyl group may include a cyclopropyl group, a cyclobutyl group, a cyclohexyl group, or the like.

In addition, the aryl group in the present disclosure means, if not specifically defined, a carbocycle aromatic radical of 6 to 20 carbon atoms and including at least one ring, and the rings may be attached or fused together in a pendant type. Particularly, the aryl group includes an aryl group of 6 to 20 carbon atoms, more particularly, 6 to 12 carbon atoms. Particular examples of the aryl group may include a phenyl group, a naphthyl group, an anthryl group, a phenanthryl group, a biphenyl group, or the like.

In addition, the arylalkyl group in the present disclosure means, if not specifically defined, a functional group (Ar—R—) obtained by bonding an aryl group (Ar) which is an aromatic hydrocarbon group to a carbon atom of a linear or branched alkyl group (R). Particularly, the arylalkyl group includes an arylalkyl group of 7 to 20 carbon atoms, more particularly, 7 to 12 carbon atoms. Particular examples of the arylalkyl group may include a benzyl group, a phenethyl group, or the like.

In addition, the alkylaryl group in the present disclosure means, if not specifically defined, a functional group (R—Ar—) obtained by bonding a linear or branched alkyl group (R) to a carbon atom of an aromatic hydrocarbon group (Ar). Particularly, the alkylaryl group includes an alkylaryl group of 7 to 20 carbon atoms, more particularly, 7 to 12 carbon atoms.

In addition, the aryloxy group in the present disclosure means, if not specifically defined, an aryl group combined with oxygen (—OAr), and in this case, the aryl group is the same as defined above. Particularly, the aryloxy group includes an aryloxy group of 6 to 20 carbon atoms, more particularly, 6 to 12 carbon atoms. Particular examples of the aryloxy group may include a phenoxy group, or the like.

In addition, the silyl group in the present disclosure means, if not specifically defined, an —$SiH_3$ radical derived from silane. At least one hydrogen atom in the silyl group may be substituted with various organic groups such as an alkyl group of 1 to 20 carbon atoms and a halogen group. Particularly, the silyl group may include a trimethylsilyl group, triethylsilyl, or the like.

In addition, the alkylamino group in the present disclosure means, if not specifically defined, a functional group obtained by substituting at least one hydrogen atom in an amino group (—$NH_2$) with an alkyl group, where the alkyl group is the same as defined above. Particularly, the alkylamino group may be —$NR_2$ (R may be a hydrogen atom or a linear or branched alkyl group of 1 to 20 carbon atoms, where both Rs are not hydrogen atoms).

In addition, the arylamino group in the present disclosure means, if not specifically defined, a functional group obtained by substituting at least one hydrogen atom in an amino group (—NH₂) with an aryl group, where the aryl group is the same as defined above.

In addition, the alkylidene group in the present disclosure means, if not specifically defined, a divalent aliphatic hydrocarbon group obtained by removing two hydrogen atoms from the same carbon atom of an alkyl group. Particularly, the alkylidene group includes an alkylidene group of 1 to 20 carbon atoms, more particularly, 1 to 12 carbon atoms. Particular examples of the alkylidene group may include a propane-2-ylidene group, or the like.

In addition, the hydrocarbyl group in the present disclosure means, if not specifically defined, a monovalent hydrocarbon group of 1 to 20 carbon atoms, which is composed of only carbon and hydrogen irrespective of the structure thereof including an alkyl group, an aryl group, an alkenyl group, an alkynyl group, a cycloalkyl group, an alkylaryl group, or an arylalkyl group. A hydrocarbylene group means a divalent hydrocarbon group of 1 to 20 carbon atoms.

In addition, the hetero hydrocarbyl group in the present disclosure may be, if not specifically defined, a hydrocarbon group including a heteroatom in place of at least one carbon atom in at least one hydrocarbon group; or a hydrocarbon group in which at least one hydrogen atom bonded to a carbon atom in at least one hydrocarbon group is substituted with a heteroatom, or a functional group including a heteroatom, where the heteroatom may be selected from the group consisting of N, O, S and Si. Particularly, the hetero hydrocarbyl group may be an alkoxy group; a phenoxy group; a carboxyl group; an acid anhydride group; an amino group; an amide group; an epoxy group; a silyl group; —[R$_a$O]$_x$R$_b$ (where R$_a$ is an alkylene group of 2 to 20 carbon atoms, R$_b$ is selected from the group consisting of a hydrogen atom, an alkyl group of 1 to 20 carbon atoms, a cycloalkyl group of 3 to 20 carbon atoms, an aryl group of 6 to 20 carbon atoms, and an arylalkyl group of 7 to 20 carbon atoms, and x is an integer of 2 to 10); a hydrocarbon group of 1 to 20 carbon atoms including at least one functional group selected from the group consisting of a hydroxyl group, an alkoxy group, a phenoxy group, a carboxyl group, an ester group, an acid anhydride group, an amino group, an amide group, an epoxy group and a silyl group (for example, a hydroxyalkyl group, an alkoxyalkyl group, a phenoxyalkyl group, an aminoalkyl group, a thioalkyl group, or the like).

Particularly, the first transition metal compound of Formula 1 may be a compound having one structure among Formulae 1a to 1c below.

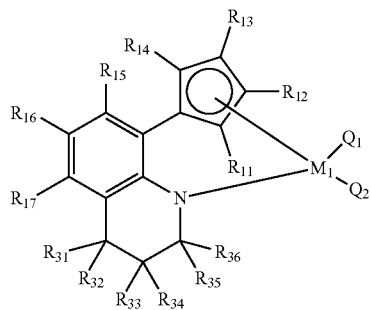

[Formula 1a]

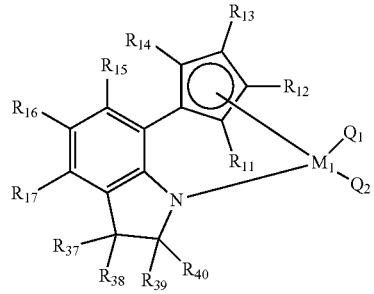

[Formula 1b]

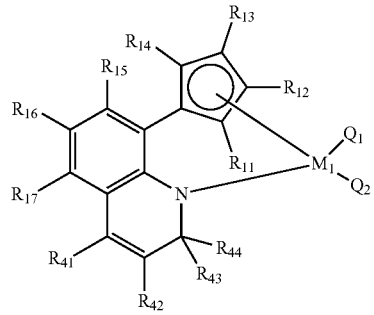

[Formula 1c]

In Formulae 1a to 1c, M₁ may be the same as defined above, and more particularly, may be Ti, Hf, or Zr.

In addition, Q₁ and Q₂ may be each independently the same as defined above, and more particularly, may be a halogen group or an alkyl group of 1 to 8 carbon atoms.

In addition, R₁₁ to R₁₄ may be the same as defined above, and more particularly, may be each independently selected from the group consisting of a hydrogen atom, a halogen group, a silyl group, an alkyl group of 1 to 8 carbon atoms, an alkenyl group of 2 to 8 carbon atoms, a cycloalkyl group of 3 to 12 carbon atoms, an aryl group of 6 to 18 carbon atoms, an alkylaryl group of 7 to 18 carbon atoms, an arylalkyl group of 7 to 18 carbon atoms, and a metalloid radical of a metal in group 14 substituted with a hydrocarbyl group of 1 to 8 carbon atoms; or at least two adjacent functional groups of R₁₁ to R₁₄ may be connected to each other to form an aliphatic saturated or unsaturated ring group of 5 to 18 carbon atoms or an aromatic ring group of 6 to 18 carbon atoms, which is unsubstituted or substituted with at least one substituent selected from the group consisting of a halogen group, an alkyl group of 1 to 8 carbon atoms, an alkenyl group of 2 to 8 carbon atoms, and an aryl group of 6 to 18 carbon atoms, and more particularly, may be an alkyl group of 1 to 4 carbon atoms.

In addition, R₁₅ to R₁₇ may be the same as defined above, and more particularly, may be each independently selected from the group consisting of a hydrogen atom, a halogen group, a silyl group, an alkyl group of 1 to 8 carbon atoms, an alkenyl group of 2 to 8 carbon atoms, a cycloalkyl group of 3 to 12 carbon atoms, an aryl group of 6 to 18 carbon atoms, an alkylaryl group of 7 to 18 carbon atoms, and an arylalkyl group of 7 to 18 carbon atoms, or at least two adjacent functional groups of R₁₅ to R₁₇ may be connected to each other to form an aliphatic saturated or unsaturated ring group of 5 to 18 carbon atoms or an aromatic ring of 6 to 18 carbon atoms, which is unsubstituted or substituted with at least one substituent selected from the group consisting of a halogen group, an alkyl group of 1 to 8 carbon atoms, an alkenyl group of 2 to 8 carbon atoms, and an aryl group of 6 to 18 carbon atoms.

In addition, $R_{31}$ to $R_{44}$ may be each independently selected from the group consisting of a hydrogen atom, a halogen group, an alkyl group of 1 to 8 carbon atoms, an alkenyl group of 2 to 8 carbon atoms, and an aryl group of 6 to 18 carbon atoms, or at least two adjacent functional groups may be connected to each other to form an aliphatic saturated or unsaturated ring group of 5 to 18 carbon atoms, or an aromatic ring of 6 to 18 carbon atoms, which is unsubstituted or substituted with at least one substituent selected from the group consisting of a halogen group, an alkyl group of 1 to 8 carbon atoms, an alkenyl group of 2 to 8 carbon atoms, and an aryl group of 6 to 18 carbon atoms, and more particularly, may be a hydrogen atom, a halogen atom, or an alkyl group of 1 to 4 carbon atoms, or at least two adjacent functional groups may be connected to each other to form an aromatic ring of 6 to 18 carbon atoms which is unsubstituted or substituted with an alkyl group of 1 to 8 carbon atoms.

More particularly, preferable first transition metal compound of Formula 1 to control electronic and steric environment around a metal may be Compounds (1-1) to (1-12) with the structures below, and any one thereof or a mixture of at least two thereof may be used.

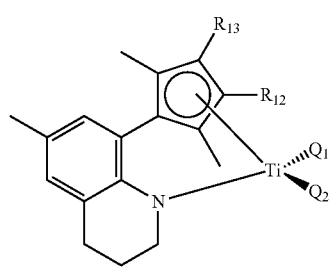
(1-1)

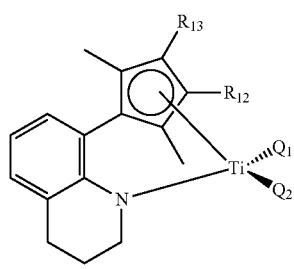
(1-2)

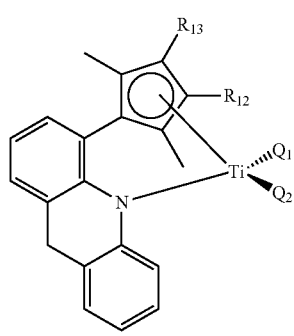
(1-3)

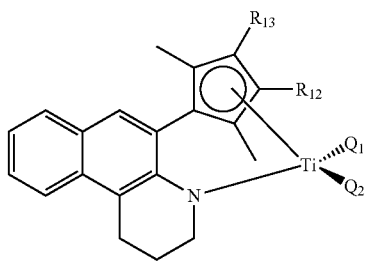
(1-4)

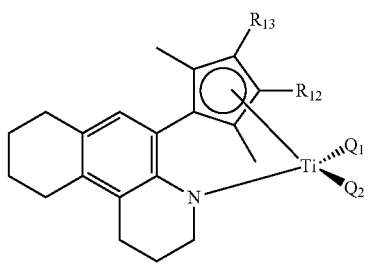
(1-5)

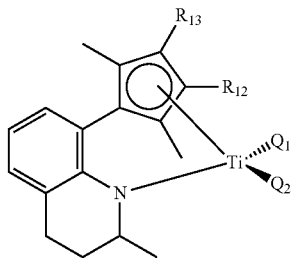
(1-6)

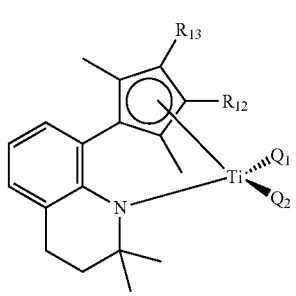
(1-7)

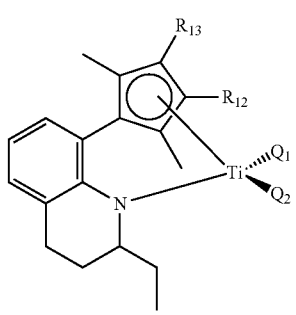
(1-8)

(1-9)

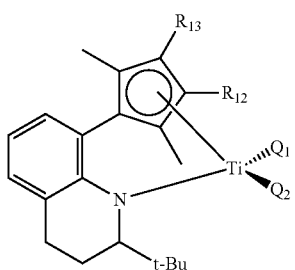

(1-10)

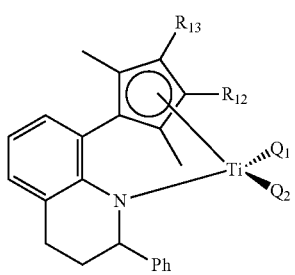

(1-11)

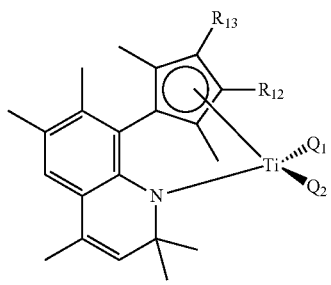

(1-12)

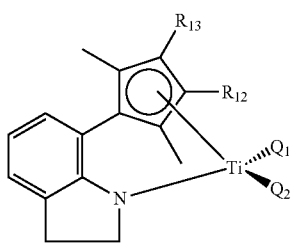

In the chemical structures above, $Q_1$, $Q_2$, $R_{12}$ and $R_{13}$ are the same as defined above.

In addition to the above-exemplified compounds, the first transition metal compound may have various structures within the defined range by Formula 1, and the compounds may show equivalent action and effects.

Meanwhile, the second transition metal compound of Formula 2 may be a compound of Formula 2a below.

[Formula 2a]

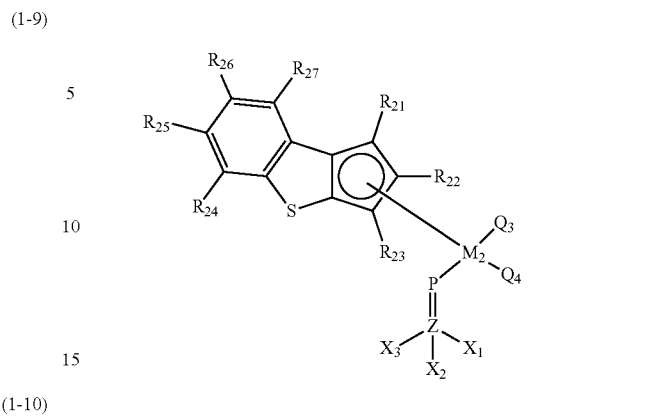

In Formula 2a, $M_2$ may be the same as defined above, and particularly, may be Ti, Hf, or Zr, $Q_3$ and $Q_4$ may be the same as defined above, and particularly, may be each independently a halogen group or an alkyl group of 1 to 8 carbon atoms, $R_{21}$ to $R_{27}$ may be the same as defined above, and more particularly, $R_{21}$ to $R_{27}$ may each independently selected from the group consisting of a hydrogen atom, a halogen group, a silyl group, an alkyl group of 1 to 8 carbon atoms, an alkenyl group of 2 to 6 carbon atoms, a cycloalkyl group of 3 to 12 carbon atoms, an aryl group of 6 to 18 carbon atoms, an alkylaryl group of 7 to 18 carbon atoms, an arylalkyl group of 7 to 18 carbon atoms, and a metalloid radical of a metal in group 14 substituted with a hydrocarbyl group of 1 to 8 carbon atoms, and more particularly, $R_{21}$ to $R_{27}$ may be each independently a hydrogen atom or an alkyl group of 1 to 8 carbon atoms, or 1 to 4 carbon atoms;

$X_1$ to $X_3$ may be the same as defined above, and more particularly, $X_1$ to $X_3$ may be each independently selected from the group consisting of a hydrogen atom, a halogen group, a silyl group, an amino group, an (alkyl of 1 to 8 carbon atoms)amino group, an alkyl group of 1 to 8 carbon atoms, an alkenyl group of 2 to 6 carbon atoms, a cycloalkyl group of 3 to 12 carbon atoms, an aryl group of 6 to 18 carbon atoms, an alkylaryl group of 7 to 18 carbon atoms, and an arylalkyl group of 7 to 18 carbon atoms; or at least two adjacent functional groups of $X_1$ to $X_3$ may be connected to each other to form a cycloalkyl group of 5 to 12 carbon atoms or an aryl group of 6 to 20 carbon atoms, which is substituted with at least one substituent selected from the group consisting of a halogen group, a silyl group, an amino group, an (alkyl of 1 to 8 carbon atoms)amino group, an alkyl group of 1 to 8 carbon atoms, an alkenyl group of 2 to 6 carbon atoms, and an aryl group of 6 to 12 carbon atoms. More particularly, $X_1$ to $X_3$ may be each independently selected from the group consisting of a halogen group, an alkyl group of 1 to 8 carbon atoms, a cycloalkyl group of 3 to 12 carbon atoms, and an aryl group of 6 to 12 carbon atoms.

More particularly, more preferable second transition metal compound of Formula 2 to control electronic and steric environment around a metal may be the following compounds, and any one thereof or a mixture of at least two thereof may be used.

(2-1)
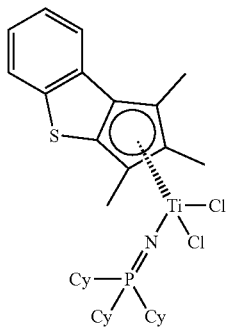

(2-2)
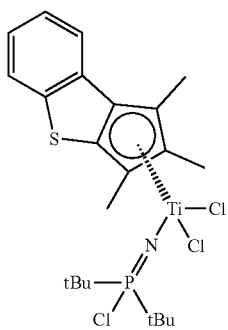

(2-3)
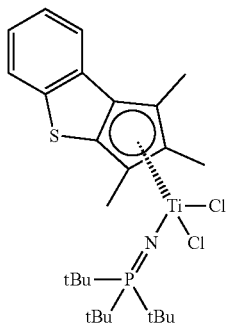

(2-4)
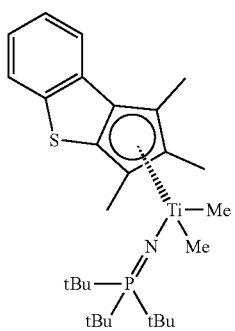

(2-5)
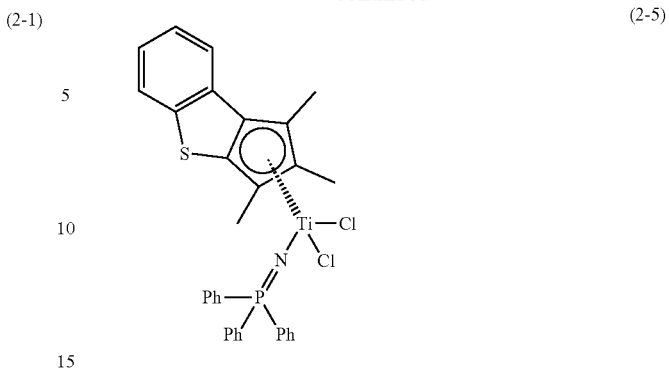

In the above chemical structures, Cy means a cyclohexyl group, tBu means a t-butyl group, Me means a methyl group, and Ph means a phenyl group.

In addition to the above-exemplified compounds, the second transition metal compound may have various structures within the defined range by Formula 2, and the compounds may show equivalent action and effects.

The first transition metal compound of Formula 1 and the second transition metal compound of Formula 2 may be prepared by using known synthetic reactions.

Meanwhile, a catalyst composition including the transition metal compounds of Formulae 1 and 2 may include the transition metal compounds of Formulae 1 and 2 in an weight ratio of 50:50 to 80:20. If the mixing ratio of the transition metal compounds of Formulae 1 and 2 deviates from the above range, the preparation of an olefin-based polymer satisfying the conditions on the physical properties defined in (1) to (4), particularly, the density conditions of (1) is difficult.

In addition, the catalyst composition may further include a cocatalyst.

The cocatalyst may be any known materials, without specific limitation, including alkylaluminoxanes, alkylaluminums or Lewis acids. Particularly, the cocatalyst may be any one selected from the group consisting of the compounds of Formulae 3 to 5 below, or a mixture of at least two thereof.

—[Al($R_{51}$)—O]a-  [Formula 3]

(In the above Formula 3, $R_5$, is each independently a halogen group, a hydrocarbyl group of 1 to 20 carbon atoms, or a hydrocarbyl group of 1 to 20 carbon atoms, substituted with halogen, and a is an integer of 2 or more)

D($R_{52}$)$_3$  [Formula 4]

(In the above Formula 4, D is aluminum or boron, and $R_{52}$ is each independently a halogen radical, a hydrocarbyl radical of 1 to 20 carbon atoms, or a hydrocarbyl radical of 1 to 20 carbon atoms, substituted with halogen)

[L-H]+[Z(A)$_4$]- or [L]+[Z(A)$_4$]-  [Formula 5]

(In the above Formula 5, L is a neutral or cationic Lewis acid, H is a hydrogen atom, Z is an element in group 13, and A is each independently an aryl group of 6 to 20 carbon atoms or alkyl group of 1 to 20 carbon atoms, where at least one hydrogen atom may be substituted with a substituent, and the substituent is a halogen group, a hydrocarbyl group of 1 to 20 carbon atoms, an alkoxy group of 1 to 20 carbon atoms, or an aryloxy group of 6 to 20 carbon atoms)

Particularly, the compound of Formula 3 may be alkylaluminoxanes, preferably, methylaluminoxane, ethylaluminoxane, isobutylaluminoxane, butylaluminoxane, or the like, and more preferably, methylaluminoxane may be used.

In addition, the compound of Formula 4 may particularly include trimethylaluminum, triethylaluminum, triisobutylaluminum, tripropylaluminum, tributylaluminum, dimethylchloroaluminum, triisopropylaluminum, tri-s-butylaluminum, tricyclopentylaluminum, tripentylaluminum, triisopentylaluminum, trihexylaluminum, trioctylaluminum, ethyldimethylaluminum, methyldiethylaluminum, tripentylaluminum, tri-p-tolylaluminum, dimethylaluminumethoxide, dimethylaluminumethoxide, trimethylboron, triethylboron, triisobutylboron, tripropylboron, tributylboron, or the like, particularly preferably, may be selected from trimethylaluminum, triethylaluminum and triisobutylaluminum.

In addition, the compound of Formula 5 may particularly include triethylammonium tetraphenylboron, tributylammonium tetraphenylboron, trimethylammonium tetraphenylboron, tripropylammonium tetraphenylboron, trimethylammonium tetra(p-tolyl)boron, trimethylammonium tetra(o,p-dimethylphenyl)boron, tributylammonium tetra(p-trifluoromethylphenyl)boron, trimethylammonium tetra(p-trifluoromethylphenyl)boron, tributylammonium tetrapentafluorophenylboron, N,N-diethylanilidiumtetraphenylboron, N,N-diethylanilidiumtetraphenylboron, N,N-diethylanilinium tetrapentafluorophenylboron, diethylammonium tetrapentafluorophenylboron, triphenylphosphoniumtetraphenylboron, triphenylphosphoniumtetraphenylboron, dimethylanilinium tetrakis(pentafluorophenyl)borate, triethylammonium tetraphenylaluminum, tributylammonium tetraphenylaluminum, trimethylammonium tetraphenylaluminum, tripropylammonium tetraphenylaluminum, trimethylammonium tetra(p-tolyl)aluminum, tripropylammonium tetra(p-tolyl)aluminum, triethylammonium tetra(o,p-dimethylphenyl)aluminum, tributylammonium tetra(p-trifluoromethylphenyl)aluminum, trimethylammonium tetra(p-trifluoromethylphenyl)aluminum, tributylammonium tetrapentafluorophenylaluminum, N,N-diethylanilinium tetraphenylaluminum, N,N-diethylanilinium tetraphenylaluminum, N,N-diethylanilinium tetrapentafluorophenylaluminum, diethylammonium tetrapentatetraphenylaluminum, triphenylphosphoniumtetraphenylaluminum, trimethylphosphoniumtetraphenylaluminum, triethylammonium tetraphenylaluminum, tributylammonium tetraphenylaluminum, trimethylammonium tetraphenylboron, tripropylammonium tetraphenylboron, trimethylammonium tetra(p-tolyl)boron, tripropylammonium tetra(p-tolyl)boron, triethylammonium tetra(o,p-dimethylphenyl)boron, trimethylammonium tetra(o,p-dimethylphenyl)boron, tributylammonium tetra(p-trifluoromethylphenyl)boron, trimethylammonium tetra(p-trifluoromethylphenyl)boron, tributylammonium tetrapentafluorophenylboron, N,N-diethylanilinium tetraphenylboron, N,N-diethylanilinium tetraphenylboron, N,N-diethylanilinium tetrapentafluorophenylboron, diethylammonium tetrapentafluorophenylboron, triphenylphosphoniumtetraphenylboron, triphenylcarbonium tetra(p-trifluoromethylphenyl)boron, triphenylcarbonium tetrapentafluorophenylboron, or the like.

In addition, the first and second transition metal compounds and the cocatalyst may be used as a supported state on a carrier. As the carrier, silica-alumina, silica-magnesia, or the like may be used, and other optional carriers known in this art may be used. In addition, the carriers may be used in a dried state at a high temperature, and the drying temperature may be, for example, from 180° C. to 800° C. If the drying temperature is less than 180° C. and excessively low, a part with an excessive amount on the carrier may react with the cocatalyst to deteriorate the performance. If the drying temperature is greater than 800° C. and excessively high, the hydroxyl content on the surface of the carrier may be decreased to reduce reaction sites with the cocatalyst.

The catalyst composition may be prepared by adding the compound of Formula 3 or Formula 4 to a first mixture of the transition metal compounds of Formulae 1 and 2 and mixing to prepare a second mixture, and adding the compound of Formula 5 thereto and mixing (first method); or by adding the compound of Formula 5 to the first mixture of the transition metal compounds of Formulae 1 and 2 and mixing (second method).

In the first method for preparing the catalyst composition, 2 to 5,000 molar ratio, more particularly, 10 to 1,000 molar ratio, further more particularly, 20 to 500 molar ratio of the compound of Formula 3 or Formula 4 may be added based on 1 mol of the first mixture of the transition metal compounds of Formulae 1 and 2. If the molar ratio of the compound of Formula 3 or Formula 4 with respect to the first mixture is less than 1:2, it is apprehended that alkylation with respect to the transition metal compounds may not be completely conducted, and if the molar ratio is greater than 1:5,000, it is apprehended that the activation of alkylated transition metal compounds may not be sufficiently accomplished due to side reactions between the excessive amount of the compound of Formula 3 or Formula 4 and the compound of Formula 5.

In addition, the compound of Formula 5 may be added in a molar ratio of 1 to 25, more particularly, 1 to 10, further more particularly, 1 to 5 based on 1 mol of the second mixture. If the molar ratio of the compound of Formula 5 with respect to the second mixture is less than 1:1, the amount of an activating agent is relatively small and the activation of the transition metal compound may not be completely conducted, thereby deteriorating the activity of a produced catalyst composition. If the molar ratio is greater than 1:25, the purity of a produced polymer may be deteriorated due to the excessive amount of the remaining compound of Formula 5.

Meanwhile, in the second method for preparing the catalyst composition, the compound of Formula 5 may be added in a molar ratio of 1 to 500, particularly, 1 to 50, more particularly, 2 to 25 based on 1 mol of the first mixture. If the molar ratio is less than 1:1, the amount of the compound of Formula 5, which is an activating agent, is relatively small, and the activation of the transition metal compounds may not be completely conducted, thereby deteriorating the activity of a produced catalyst composition. If the molar ratio is greater than 1:500, the activation of the transition metal compounds may be completely conducted, but the purity of a produced polymer may be deteriorated due to the excessive amount of the remaining compound of Formula 5.

In addition, the catalyst composition may further include an additive.

Particularly, the additive may be a compound containing at least one heteroatom selected from the group consisting of O, S, Se, N, P and Si. In addition, the compound containing a heteroatom may be a five- or six-member aromatic cyclic compound containing a heteroatom, a heterocycle compound such as heterocycloalkene and heterocycloalkene; or alkane containing a heteroatom such as alkane containing an amine group or an ether group. The compound containing a heteroatom may be substituted with one or two or more substituents selected from the group consisting of a methyl group, a phenyl group and a benzyl group. More particularly, examples of the compound containing a heteroatom may include pyridine, 3,5-dimethylpyridine, 2,4,6-trimethylpyridine, 2,6-dimethylpyridine, 2,4-dimethylpyridine, thiophene, 2-methylthiophene, 2,3-dimethylthiophene, piperidine, phosphinene, pyrrole, 2-methylpyrrole, aniline, p-toluidine, tetrahydrofuran, 2,3-dimethyltetrahydrofuran, 2,5-tetrahydrofuran, 3,4-dihydro-2H-pyrene, furan, 2-methylfuran, 2,3-dimethylfuran, 2,5-dimethylfuran, diethyl ether, methyl t-butyl ether or triethylamine, and any one thereof or a mixture of at least two thereof may be used.

Meanwhile, monomers used for preparing the olefin-based polymer may particularly include an alpha-olefin-based monomer, a cyclic olefin-based monomer, a diene olefin-based monomer, a triene olefin-based monomer, a styrene-based monomer, or the like.

The alpha-olefin-based monomer may be an aliphatic olefin of 2 to 12 carbon atoms, or 2 to 8 carbon atoms, and may particularly include ethylene, propylene, 1-butene, 1-pentene, 3-methyl-1-butene, 1-hexene, 4-methyl-1-pentene, 3-methyl-1-pentene, 1-heptene, 1-octene, 1-decene, 1-undecene, 1-dodecene, 1-tetradecene, 1-hexadecene, 1-itocene, 4,4-dimethyl-1-pentene, 4,4-diethyl-1-hexene, 3,4-dimethyl-1-hexene, or the like.

In addition, the cyclic olefin-based monomer may be cyclic olefin of 3 to 24 carbon atoms, or 3 to 18 carbon atoms, and may particularly include cyclopentene, cyclobutene, cyclehexene, 3-methylcyclohexene, cyclooctene, tetracyclodecene, octacyclodecene, dicyclopentadiene, norbornene, 5-methyl-2-norbornene, 5-ethyl-2-norbornene, 5-isobutyl-2-norbornene, 5,6-dimethyl-2-norbornene, 5,5,6-trimethyl-2-norbornene, ethylenenorbornene, or the like.

In addition, the diene- and triene-based monomers may be a polyene of 4 to 26 carbon atoms, having two or three double bonds, and may particularly include 1,3-butadiene, 1,4-pentadiene, 1,4-hexadiene, 1,5-hexadiene, 1,9-decadiene, 2-methyl-1,3-butadiene, or the like.

In addition, the styrene-based monomer may be styrene; or styrene substituted with an alkyl group of 1 to 10 carbon atoms, an alkoxy group of 1 to 10 carbon atoms, a halogen group, an amino group, a silyl group, a haloalkyl group, or the like.

In addition, a polymerization reaction for preparing the olefin-based polymer may be conducted via a solution phase, slurry phase, a bulk phase or a gas phase polymerization process, because a catalyst composition is present in a supported state on a carrier, or an insoluble particulate state of a carrier as well as a homogeneous solution state. However, in the present invention, the solution polymerization process is applied. Polymerization conditions during the solution polymerization may be diversely changed according to the state of a catalyst used (homogeneous phase or nonhomogeneous phase (supported type)), a polymerization method (solution polymerization, slurry polymerization, or gas polymerization), desired polymerization results or a polymer type.

The solution polymerization may be conducted in a hydrocarbon-based solvent. The solvent may particularly be an aliphatic hydrocarbon-based solvent of 5 to 12 carbon atoms such as pentane, hexane, heptane, or the like, a hydrocarbon solvent which is substituted with a chlorine atom such as dichloromethane and chlorobenzene, an aromatic hydrocarbon solvent such as benzene and toluene. However, examples of the solvent are not limited thereto, and all solvents used in the art may be applied. The solvent used may preferably be treated with a small amount of alkylaluminums to remove a trace amount of water or air acting as a catalytic poison, and a cocatalyst may be further included. The alkylaluminums may include trialkylaluminums, dialkyl aluminum halides, alkyl aluminum dihalides, aluminum dialkyl hydrides or alkyl aluminum sesqui halides, or the like. More particularly, $Al(C_2H_5)_3$, $Al(C_2H_5)_2H$, $Al(C_3H_7)_3$, $Al(C_3H_7)_2H$, $Al(i-C_4H_9)_2H$, $Al(C_8H_{17})_3$, $Al(C_{12}H_{25})_3$, $Al(C_2H_5)(C_{12}H_{25})_2$, $Al(i-C_4H_9)(C_{12}H_{25})_2$, $Al(i-C_4H_9)_2H$, $Al(i-C_4H_9)_3$, $(C_2H_5)_2AlCl$, $(i-C_3H_9)_2AlCl$, $(C_2H_5)_3Al_2Cl_3$, or the like may be used. These organic aluminum compounds may be continuously injected into each reactor and may be injected by a molar ratio of about 0.1 to 10 mol per 1 kg of a reaction medium which is injected into the reactor for the appropriate removal of water.

In addition, the polymerization reaction during preparing the olefin-based polymer may be continuously conducted in a single reactor.

In addition, the polymerization reaction may be conducted in a temperature range of 120° C. to 250° C., particularly, 130° C. to 200° C. In addition, the pressure during polymerization may be from about 1 bar to about 150 bar, particularly, from about 1 bar to about 120 bar, more particularly, from about 10 bar to about 120 bar.

In addition, the olefin-based polymer prepared by the above-described preparation method may be surface treated with talc, or a Ca-based or Si-based inorganic material according to a common method. Accordingly, the olefin-based polymer according to the present invention may further include a coating layer including talc, or a Ca-based or Si-based inorganic material at the surface thereof.

The olefin-based polymer prepared by the preparation method and satisfying the physical property conditions may exhibit improved impact strength without degrading mechanical properties such as tensile strength. Particularly, the olefin-based polymer may have a maximum tensile strength of 160 kgf/cm$^2$ to 200 kgf/cm$^2$ when taking measurements of maximum tensile strength according to ASTM D638 (conditions: 50 mm/min). In addition, impact strength may be 55 kgf·m/m or more at 25±5° C. when taking measurements of impact strength according to ASTM D256.

More particularly, in the polypropylene-based composite material according to an embodiment of the present invention, the olefin-based polymer may be an ethylene α-olefin copolymer satisfying the conditions of (b11) to (b14) below, and in this case, the amount of the ethylene α-olefin copolymer may be from 3 wt % to 50 wt %, more particularly, from 10 wt % to 50 wt %, further more particularly, from 10 wt % to 20 wt % based on the total amount of the polypropylene-based composite material, thereby attaining excellent mechanical strength and markedly improved impact strength properties at a low temperature:

(b11) density: from 0.850 g/cc to 0.910 g/cc, (b12) melt index (190° C., 2.16 kg load conditions): from 0.1 g/10 min to 100 g/10 min, (b13) molecular weight distribution: from 1.5 to 3.0, and (b14) when taking measurements of temperature rising elution fractionation, two peaks are shown in a temperature range of −20° C. to 120° C., and a relation of T(90)−T(50) ≥60° C. is satisfied (where T(90) is a temperature at which 90 wt % of the olefin-based polymer is eluted, and T(50) is a temperature at which 50 wt % of the olefin-based polymer is eluted).

In addition, in the polypropylene-based composite material according to an embodiment of the present invention, the olefin-based polymer may be an ethylene α-olefin copolymer satisfying the conditions of (b21) to (b25) below, and in this case, the amount of the ethylene α-olefin copolymer may be from 3 wt % to 25 wt %, more particularly, from 9 wt % to 15 wt % based on the total amount of the polypropylene-based composite material, thereby attaining excellent impact strength and mechanical strength properties such as hardness, and further, improving transparency:

(b21) density: from 0.860 g/cc to 0.910 g/cc, (b22) melt index (190° C., 2.16 kg load conditions): from 0.1 g/10 min to 200 g/10 min, (b23) molecular weight distribution: from 1.5 to 3.0, (b24) when taking measurements of temperature rising elution fractionation, two peaks are shown in a temperature range of −20° C. to 120° C., and a relation of T(90)−T(50) ≥60° C. is satisfied (where T(90) is a temperature at which 90 wt % of the olefin-based polymer is eluted, and T(50) is a temperature at which 50 wt % of the olefin-based polymer is eluted), and (b25) weight average molecular weight: from 10,000 g/mol to 500,000 g/mol, more particularly, from 10,000 g/mol to 50,000 g/mol.

In this case, the ethylene α-olefin copolymer may be a uniformly branched copolymer, and the ethylene α-olefin copolymer may be linear or substantially linear.

More particularly, the ethylene α-olefin copolymer may be an ethylene/octene elastomer satisfying the above-described physical conditions of (b21)-(b25).

Meanwhile, the polypropylene-based composite material having the above-described constitution according to an embodiment of the present invention may include each constituent component in an appropriate amount so that a rubber composition introducing the same satisfies its use and consequently required physical properties. Particularly, in the present invention, the polypropylene-based composite material may include the polypropylene and an olefin-based polymer in an weight ratio of 50:50 to 90:10. If the amount of the olefin-based polymer is less than the mixing ratio, impact strength at a low temperature may be degraded, and if the mixing ratio is greater than the mixing ratio, tensile strength and hardness may be degraded. In consideration of remarkable improving effects according to the control of the mixing ratio of the polypropylene and the olefin-based polymer, the polypropylene and the olefin-based polymer may more particularly be used in an weight ratio of 70:30 to 85:15.

In addition, the polypropylene may be included in an amount of satisfying the mixing ratio conditions, and at the same time, in an amount of 50 wt % 97 wt %, more particularly, 50 wt % to 90 wt % based on the total amount of the polypropylene composite material.

In consideration of remarkable improving effects according to the kind of polymers constituting a polypropylene composite material and the optimal combination configuration of the physical properties thereof, the polypropylene composite material according to an embodiment of the present invention may include (A1) polypropylene; and (B1) an olefin-based polymer satisfying the conditions of the following (b11) to (b14):

(b11) density (d): from 0.850 g/cc to 0.910 g/cc, (b12) melt index (MI, 190° C., 2.16 kg load conditions): from 0.1 g/10 min to 100 g/10 min, (b13) molecular weight distribution (MWD): from 1.5 to 3.0, and (b14) when taking measurements of temperature rising elution fractionation (TREF), two peaks are shown in a temperature range of −20° C. to 120° C. and a relation of T(90)−T(50)≥60° C. is satisfied (where T(90) is a temperature at which 90 wt % of the olefin-based polymer is eluted, and T(50) is a temperature at which 50 wt % of the olefin-based polymer is eluted).

In addition, the polypropylene composite material according to another embodiment of the present invention may include (A2) from 75 wt % to 97 wt % of at least one random propylene copolymer having a DSC melting point in a range of 120° C. to 160° C. and a melt flow rate in a range of 5 g/10 min to 120 g/10 min; and (B2) from 3 wt % to 25 wt % of an ethylene α-olefin copolymer satisfying the following conditions of (b21) to (b25):

(b21) density: from 0.860 g/cc to 0.910 g/cc, (b22) melt index (190° C., 2.16 kg load conditions): from 0.1 g/10 min to 200 g/10 min, (b23) molecular weight distribution (MWD): from 1.5 to 3.0, (b24) when taking measurements of temperature rising elution fractionation (TREF), two peaks are shown in a temperature range of −20° C. to 120° C. and a relation of T(90)−T(50)≥60° C. is satisfied (where T(90) is a temperature at which 90 wt % of the olefin-based polymer is eluted, and T(50) is a temperature at which 50 wt % of the olefin-based polymer is eluted), and (b25) weight average molecular weight: from 10,000 g/mol to 500,000 g/mol.

in addition, this case, the polypropylene composite material may further include of at least one propylene α-olefin hybrid polymer having a DSC melting point of less than 1100, a fusion heat in a range of less than 50 J/g, a crystallinity in a range of 1 wt % to 40 wt %, and a melt flowing rate in a range of less than 80 g/10 min in an amount of 5 wt % to 15 wt % based on the total amount of the polypropylene-based composite material, together with the polypropylene (A2) and the olefin-based polymer (B2). If the propylene α-olefin hybrid polymer is further included in the above-described amount, hardness properties may be even further improved.

The propylene α-olefin hybrid polymer may be directly prepared so as to satisfy the physical properties by using a common polymerization reaction, or may be commercially purchased and used. Particular examples may include VERSIFY™ (manufactured by Dow Chemical Co.), and VISTAMAXX™ (manufactured by Exxon Mobil Chemical Co.).

In addition, the polypropylene-based composite material according to an embodiment of the present invention may selectively further include an inorganic filler to improve the mechanical properties of the polypropylene-based composite material together with the polypropylene and the olefin-based polymer.

The inorganic filler may particularly be a powder-type filler, a flake-type filler, a fiber-type filler, or a balloon-type filler, and any one thereof or a mixture of at least two thereof may be used. Particularly, the powder-type filler may include natural silicic acids or silicates such as fine powdered talc, kaolinite, a plastic clay, and sericite; carbonates such as precipitated calcium carbonate, heavy calcium carbonate, and magnesium carbonate; hydroxides such as aluminum hydroxide, and magnesium hydroxide; oxides such as zinc oxide, magnesium oxide, and titanium oxide; synthetic silicic acids or silicates such as calcium silicate hydrate, aluminum silicate hydrate, silicic acid hydrate, and anhydrous silicic acid; silicon carbide, or the like. The flake-type filler may include mica. The fiber-type filler may include alkaline magnesium sulfate whisker, calcium titanate whisker, aluminum borate whisker, sepiolite, processed mineral fiber (PMF), potassium titanate, or the like. The balloon-type filler may include glass balloon, or the like. Among them, talc may be used.

In addition, the inorganic filler may be surface treated to improve the strength properties and molding processability of the polypropylene composite material.

Particularly, the inorganic filler may be physically or chemically surface treated using a surface treating agent such as a silane coupling agent, a higher fatty acid, a fatty acid metal salt, an unsaturated organic acid, an organic titanate, a resin acid, a polyethylene glycol, or the like.

In addition, the inorganic filler may have an average particle diameter ($D_{50}$) of 1 µm to 20 µm, more particularly, 7 µm to 15 µm. If the average particle diameter of the inorganic filler is less than 1 µm, homogeneous dispersion during mixing the polypropylene and the olefin-based polymer may be difficult due to the agglomeration between inorganic filler particles. As a result, the improving effects of the mechanical properties of the polypropylene-based composite material may be insignificant. If the average particle diameter of the inorganic filler is greater than 20 µm, the physical properties of a rubber composition may be degraded due to the decrease of the dispersibility of the inorganic filler itself.

In the present invention, the average particle diameter ($D_{50}$) of the inorganic filler may be defined as a particle diameter at the standard of 50% of particle diameter distribution. In the present invention, the average particle diameter ($D_{50}$) of the inorganic filler particles may be measured via, for example, observation using an electron microscope such as scanning electron microscopy (SEM) and a field emission scanning electron microscopy (FE-SEM), or via a laser diffraction method. If measurement is taken using the laser diffraction method, inorganic filler particles are, more particularly, dispersed in a dispersion medium and introduced in a commercially available laser diffraction particle size measurement apparatus (for example, Microtrac MT 3000), and the average particle diameter ($D_{50}$) may be computed at the standard of 50% of particle diameter distribution in the measurement apparatus.

The inorganic filler may be included in an amount of 0.1 parts by weight to 40 parts by weight based on 100 parts by weight of the polypropylene. If the amount of the inorganic filler in the polypropylene composite material is less than 0.1 parts by weight based on 100 parts by weight of the polypropylene, improving effects according to the inclusion of the inorganic filler may be insignificant, and if the amount is greater than 40 parts by weight, it is apprehended that the processability of the polypropylene composite material may be degraded. More particularly, the inorganic filler may be included in an amount of 0.1 wt % to 20 wt % based on the total amount of the polypropylene composite material.

The polypropylene-based composite material satisfying the above-described constitution and amount conditions according to an embodiment of the present invention may be prepared by adding polypropylene and selectively an inorganic filler to an olefin-based polymer and heat treating. In this case, the kind and amount of the polypropylene are the same as described above.

A mixing process may be conducted according to a common method. Particularly, the mixing process may be conducted using a super mixer or a ribbon mixer.

In addition, during the mixing process, an additive such as an antioxidant, a thermal stabilizer, an ultraviolet stabilizer, and an antistatic agent may be further included if needed. A small amount of an adhesive resin or an additive having a polar group may be selectively further used in an appropriate amount range to improve coatability.

In addition, the heat treatment process may be conducted at a temperature from the melting point of polypropylene to 210° C. The heat treatment process may be conducted using various machines for mixing and processing such as a twin-screw extruder, a single-screw extruder, a roll-mill, a kneader, and a banbury mixer.

Since the polypropylene composite material according to an embodiment of the present invention, prepared by the preparation method described above uses different kinds of olefin-based polymers an appropriate combination to improved the impact strength of the polypropylene composite material, dispersibility of polypropylene may be increased, thereby improving the impact strength of the polypropylene composite material without degrading mechanical properties such as tensile strength.

Particularly, the polypropylene composite material may have the maximum tensile strength of 170 $kgf/cm^2$ to 200 $kgf/cm^2$ when taking measurements of the maximum tensile strength according to ASTM D638 (conditions: 50 mm/min). In addition, the polypropylene-based composite material may have impact strength at a low temperature (−30±5° C.) of 5 kgf·m/m or more, particularly, 5 kgf·m/m to 10 kgf·m/m, more particularly, 5.5 kgf·m/m to 9 kgf·m/m when taking measurements according to an ASTM D256 method. In addition, the polypropylene-based composite material may have impact strength at room temperature (23±5° C.) of 40 kgf·m/m or more, particularly, 50 kgf·m/m to 70 kgf·m/m when taking measurements according to an ASTM D256 method.

Accordingly, the polypropylene-based composite material according to an embodiment of the present invention may be used for hollow molding, extrusion molding or injection molding in diverse fields and uses including wrapping, construction, daily supplies, or the like, in addition to as a material of an automobile, a wire, a toy, a fiber, a medicine, or the like. Particularly, since tensile properties and impact strength at room temperature and at a low temperature are excellent, and physical properties such as heat resistance and rigidity are very excellent, the polypropylene-based composite material may be used for automotive interior or exterior parts.

According to another embodiment of the present invention, a molded article and an automobile part prepared by using a polypropylene-based composite material satisfying the physical property conditions are provided.

The molded article may particularly include a blow molding molded article, an inflation molded article, a cast molded article, an extrusion laminate molded article, an extrusion molded article, a foamed molded article, an injection molded article, a sheet, a film, a fiber, a monofilament, a non-woven fabric, or the like.

In addition, the automobile part may include interior or exterior materials for an automobile.

Mode for Carrying out the Invention

Hereinafter, the present invention will be explained in particular with reference to preferred embodiments. However, the following embodiments are only illustration, and the scope of the present invention is not limited thereto.

SYNTHETIC EXAMPLE

A compound (1.30 g, 2.37 mmol) represented by Formula (i) below was dissolved in toluene (20 ml), and MeMgBr (1.62 ml, 4.86 mmol, 2.05 eq.) was slowly added thereto dropwisely at room temperature (23° C.). After that, stirring was conducted at room temperature for 12 hours. After confirming the disappearance of starting materials via NMR, a toluene solvent was removed via vacuum filtration, and a reaction mixture was dissolved in hexane (30 ml). Then, a solid was removed by filtration, and a hexane solvent in the solution thus obtained was removed via vacuum filtration to obtain a transition metal compound of Formula (ii) below.

$^1$H NMR (500 MHz, in C$_6$D$_6$): 7.62 (d, 1H), 7.43 (d, 1H), 7.13 (t, 1H), 7.03 (t, 1H), 2.30 (s, 3H), 2.09 (s, 3H), 2.02 (s, 3H), 1.28 (d, 27H), −0.24 (s, 3H), −0.27 (s, 3H)

PREPARATION EXAMPLE 1

Preparation of Olefin Polymer

Into a 1.5 L autoclave continuous process reactor, a hexane solvent (4.8 kg/h) and 1-octene (0.55 kg/h) were injected, and the temperature of the upper end portion of the reactor was pre-heated to 160° C. A triisobutylaluminum compound (0.05 mmol/min), [(1,2,3,4-tetrahydroquinolin-8-yl)tetramethylcyclopentadienyl-η5,κ-N]titanium dimethyl (0.5 μmol/min) as a first transition metal compound (A), a second transition metal compound of Formula ii (0.5 μmol/min, mixing weight ratio of first and second transition metal compounds=5:5), which was prepared in the synthetic example, and a dimethylanilinium tetrakis(pentafluorophenyl)borate cocatalyst (1.5 μmol/min) were injected into the reactor at the same time. Then, ethylene (0.87 kg/h) was injected into the autoclave reactor, and the pressure of 89 bar at 160° C. was maintained for 30 minutes in a continuous process, and a copolymerization reaction was conducted to produce a copolymer. After that, a remaining ethylene gas was exhausted out, and a polymer solution was dried in a vacuum oven for at least 12 hours. Physical properties were measured.

PREPARATION EXAMPLE 2

Preparation of Olefin Polymer

An olefin-based polymer was prepared by conducting the same method described in Example 1 except for using 1.42 kg/h of 1-octene in Preparation Example 1.

PREPARATION EXAMPLE 3

Preparation of Olefin Polymer

An olefin-based random copolymer was prepared by conducting the same method described in Preparation Example 1 except for using 1.19 kg/h of 1-octene in Preparation Example 1.

PREPARATION EXAMPLE 4

Preparation of Olefin Polymer

An olefin-based random copolymer was prepared by conducting the same method described in Preparation Example 1 except for using 1.39 kg/h of 1-octene in Preparation Example 1.

PREPARATION EXAMPLE 5

Preparation of Olefin Polymer

An olefin-based random copolymer was prepared by conducting the same method described in Example 1 except for using 1.50 kg/h of 1-octene in Preparation Example 1.

PREPARATION EXAMPLE 6

Preparation of Olefin Polymer

An olefin-based random copolymer was prepared by conducting the same method described in Preparation Example 1 except for using 1.69 kg/h of 1-octene in Preparation Example 1.

PREPARATION EXAMPLE 7

Preparation of Olefin Polymer

An olefin-based random copolymer was prepared by conducting the same method described in Preparation Example 1 except for using 1.58 kg/h of 1-octene in Preparation Example 1.

EXAMPLE 1

Preparation of Polypropylene-based Composite Material

To 20 wt % of the olefin polymer prepared in Preparation Example 1, 80 wt % of a polypropylene impact copolymer (SEETE M1600, LG Chem. Ltd.) having a melt index of 25 g/10 min was added, and then, melted and mulled using a twin-screw extruder to prepare a polypropylene composite material compound in a pellet phase. In this case, the twin-screw extruder had a diameter of 25 and a ratio of diameter and length of 40, and the conditions were set to a barrel temperature of 160° C. to 210° C., a screw rotation rate of 250 rpm, and an extrusion amount of 25 kr/hr.

EXAMPLES 2 TO 7

Preparation of Polypropylene-based Composite Materials

Polypropylene-based composite materials were prepared by conducting the same method described in Example 1 except for using each olefin polymer prepared in Preparation Examples 2 to 7.

EXAMPLE 8

Preparation of Polypropylene-based Composite Material

A Polypropylene-based composite material was prepared by conducting the same method described in Example 1 except for using 20 parts by weight of the olefin polymer prepared in Preparation Example 1, 60 parts by weight of a polypropylene impact copolymer (SEETE™ M1600, LG Chem. Ltd.), and 20 parts by weight of talc (KCNAP-400™, Coats Co.) (average particle diameter (D50)=11.0 μm).

EXAMPLE 9

Preparation of Polypropylene-based Composite Material

A Polypropylene-based composite material was prepared by conducting the same method described in Example 1 except for using 10 parts by weight of the olefin polymer prepared in Preparation Example 1, 90 parts by weight of FORMOLENE™ 7320B (manufactured by Formosa plastics Co.) (density=0.90 g/cc, MRF=20 g/10 min@230° C.) as polypropylene.

EXAMPLE 10

Preparation of Polypropylene-based Composite Material

A Polypropylene-based composite material was prepared by conducting the same method described in Example 1 except for using 10 parts by weight of the olefin polymer prepared in Preparation Example 1, 90 parts by weight of BRASKEM™ PP R7021-50RNA (manufactured by Braskem american Inc. Co.) (density=0.90 g/cc, MFR=50 g/10 min@230° C.) as polypropylene.

EXAMPLE 11

Preparation of Polypropylene-based Composite Material

A Polypropylene-based composite material was prepared by conducting the same method described in Example 1 except for using 5 parts by weight of the olefin polymer prepared in Preparation Example 1, 90 parts by weight of a propylene/ethylene copolymer, BRASKEM™ PP R7021-50RNA (manufactured by Braskem american Inc. Co.) (density=0.90 g/cc, MFR=50 g/10 min@230° C.) as polypropylene, and additionally, 5 parts by weight of VERSIFY™ 4301 (manufactured by Dow chemical Co.) (density=0.867 g/cc, MFR=25 g/10 min@230° C.), which is propylene/ethylene copolymer, as a propylene α-olefin hybrid polymer.

COMPARATIVE EXAMPLE 1

Preparation of Polypropylene-based Composite Material

A Polypropylene-based composite material was prepared by conducting the same method described in Example 1 except for using EG8200™ (manufactured by Dow chemical Co.) as an ethylene-1-octene copolymer instead of the olefin-based polymer in Example 1.

COMPARATIVE EXAMPLE 2

Preparation of Polypropylene-based Composite Material

A Polypropylene-based composite material was prepared by conducting the same method described in Example 1 except for using LC670™ (manufactured by LG chem. Ltd.) as an ethylene-1-octene copolymer prepared using only one kind of a metallocene catalyst instead of the olefin-based polymer in Example 1.

COMPARATIVE EXAMPLE 3

Preparation of Polypropylene-based Composite Material

A Polypropylene-based composite material was prepared by conducting the same method described in Example 1 except for using EG8407™ (manufactured by Dow chemical Co.) as an ethylene-1-octene copolymer instead of the olefin-based polymer in Example 1.

COMPARATIVE EXAMPLE 4

Preparation of Polypropylene-based Composite Material

A Polypropylene-based composite material was prepared by conducting the same method described in Example 1 except for using ST508™ (manufactured by LG Chem. Ltd.) as LLDPE prepared using only one kind of Zeigler-Natta catalyst instead of the olefin-based polymer in Example 1.

COMPARATIVE EXAMPLE 5

Preparation of Polypropylene-based Composite Material

A Polypropylene-based composite material was prepared by conducting the same method described in Example 1 except for using 20 parts by weight of EG8200™ (manufactured by Dow chemical Co.) as an ethylene-1-octene copolymer, 60 parts by weight of SEETE™ M1600 (manufactured by LG Chem. Ltd.) as a polypropylene impact copolymer, and 20 parts by weight of talc (KCNAP-400™, manufactured by Coats Co.) (average particle diameter ($D_{50}$)=11.0 μm).

EXPERIMENTAL EXAMPLE 1

Evaluation of Physical Properties of Olefin-based Polymer (I)

Various physical properties of the olefin-based polymers prepared in Preparation Examples 1 to 7 and Comparative Examples 1 to 4 were measured and evaluated by the methods described below.

(1) Density of a polymer (g/cc); measured according to ASTM D-792.

(2) Melt index of a polymer (MI, g/10 min); measured according to ASTM D-1238 (condition E, 190° C., 2.16 kg load).

(3) Weight average molecular weight (Mw, g/mol) and molecular weight distribution (MWD); Each of a number average molecular weight (Mn) and a weight average molecular weight (Mw) was measured using gel permeation chromatography (GPC), and the weight average molecular weight was divided by the number average molecular weight to calculate molecular weight distribution.

(4) Temperature Rising Elution Fractionation (TREF)

TREF was measured using a TREF machine of Polymer-Char Co. using an o-dichlorobenzene solvent in a range of −20° C.-120° C.

In detail, 40 mg of a polymer sample was dissolved in 20 ml of an o-dichlorobenzene solvent at 135° C. for 30 minutes and stabilized at 95° C. for 30 minutes. The solution thus obtained was introduced in a TREF column and cooled to −20° C. in a temperature decreasing rate of 0.5° C./min, and the temperature was kept for 2 minutes. Then, the temperature was increased by heating from −20° C. to 120° C. in a temperature increasing rate of 1° C./min, and an o-dichlorobenzene solvent was flowed in the column in a flow rate of 0.5 ml/min. The elution amount of a polymer according to the elution temperature, the elution amounts at 50° C. and 90° C., and the accumulated elution amount via purging and at 10° C. were measured.

Figure 2:
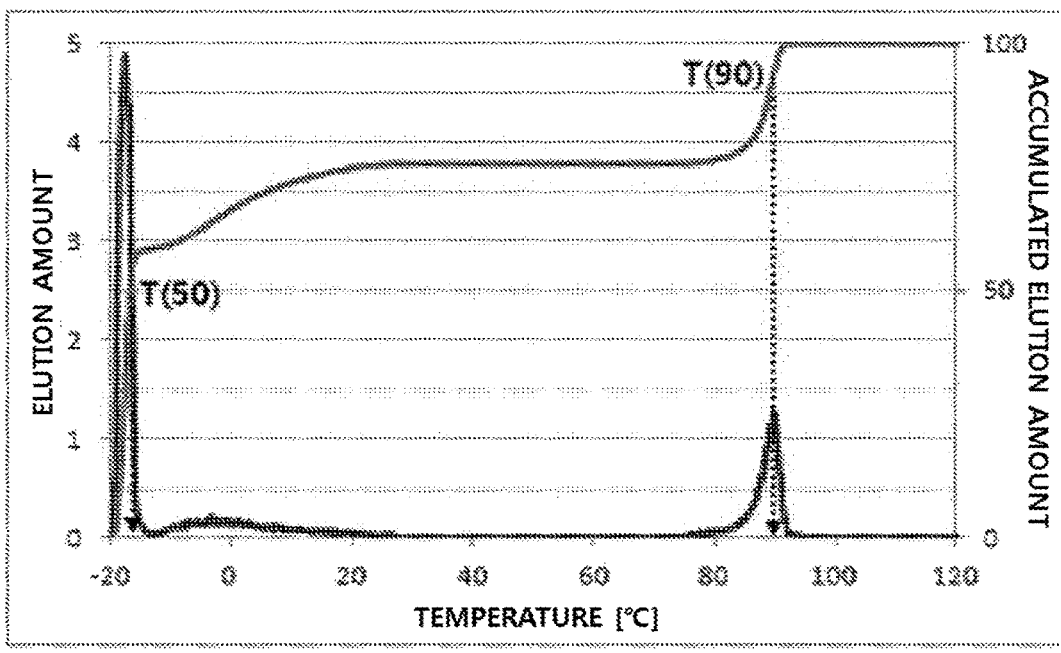
FIG. 2 illustrates a temperature rising elution fractionation (TREF) graph of an olefin-based polymer prepared in Preparation Example 2.
Figure 3:
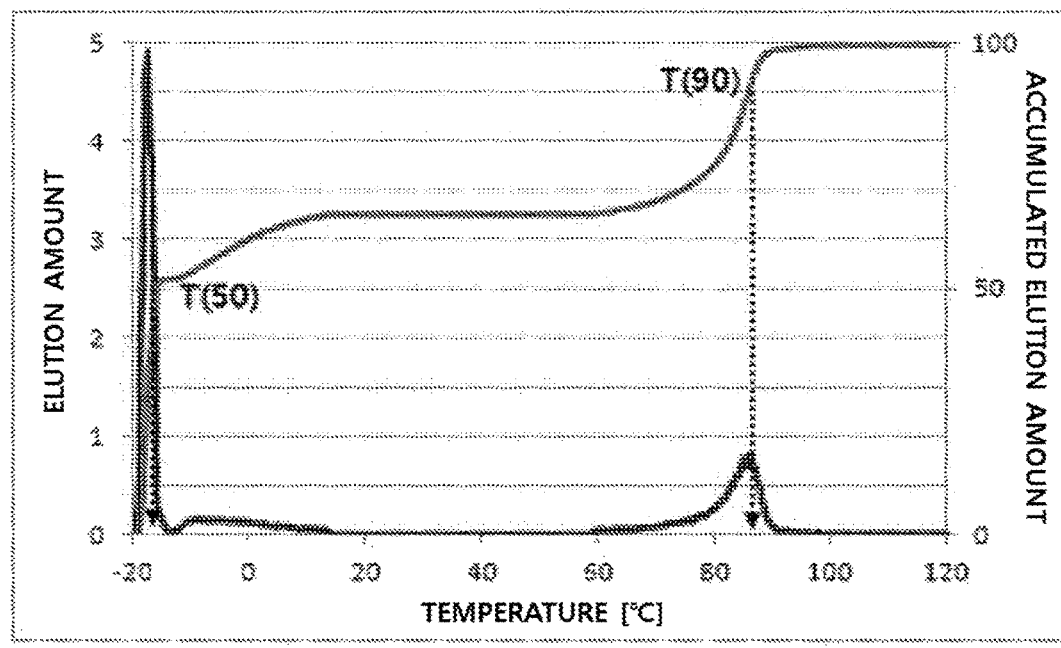
FIG. 3 illustrates a temperature rising elution fractionation (TREF) graph of an olefin-based polymer prepared in Preparation Example 3.
Figure 4:
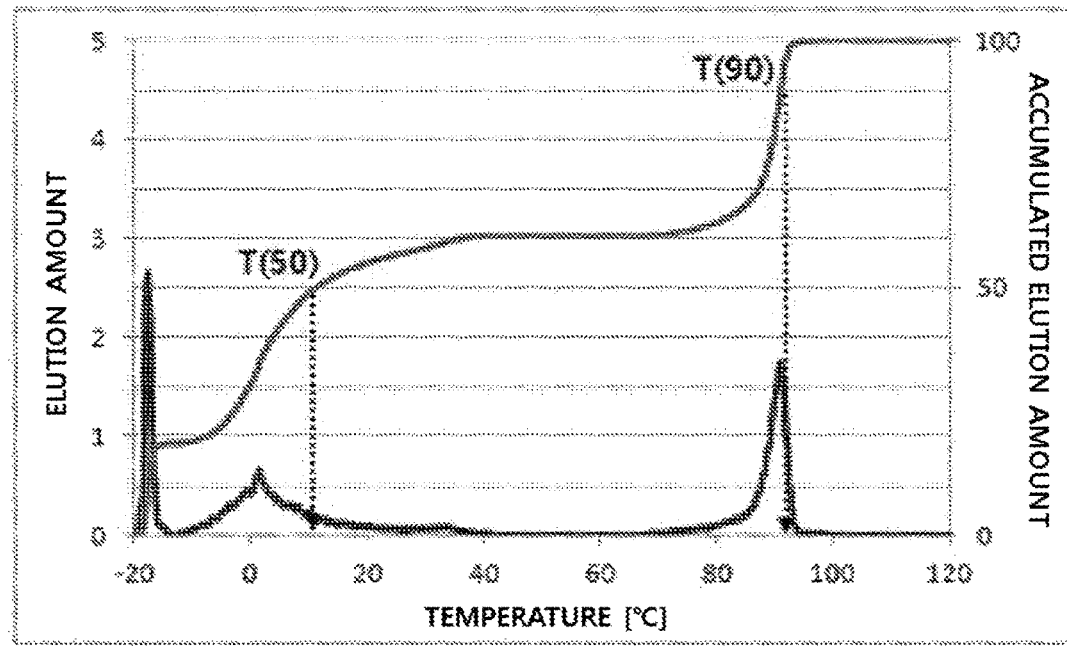
FIG. 4 illustrates a temperature rising elution fractionation (TREF) graph of an olefin-based polymer prepared in Preparation Example 4.
Figure 5:
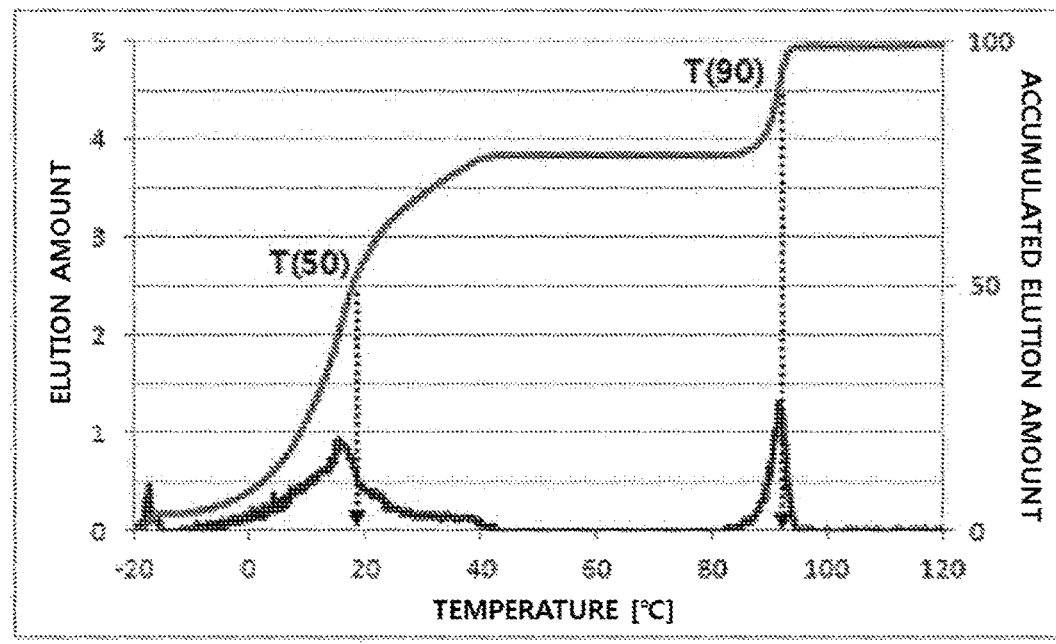
FIG. 5 illustrates a temperature rising elution fractionation (TREF) graph of an olefin-based polymer prepared in Preparation Example 5.
Figure 6:
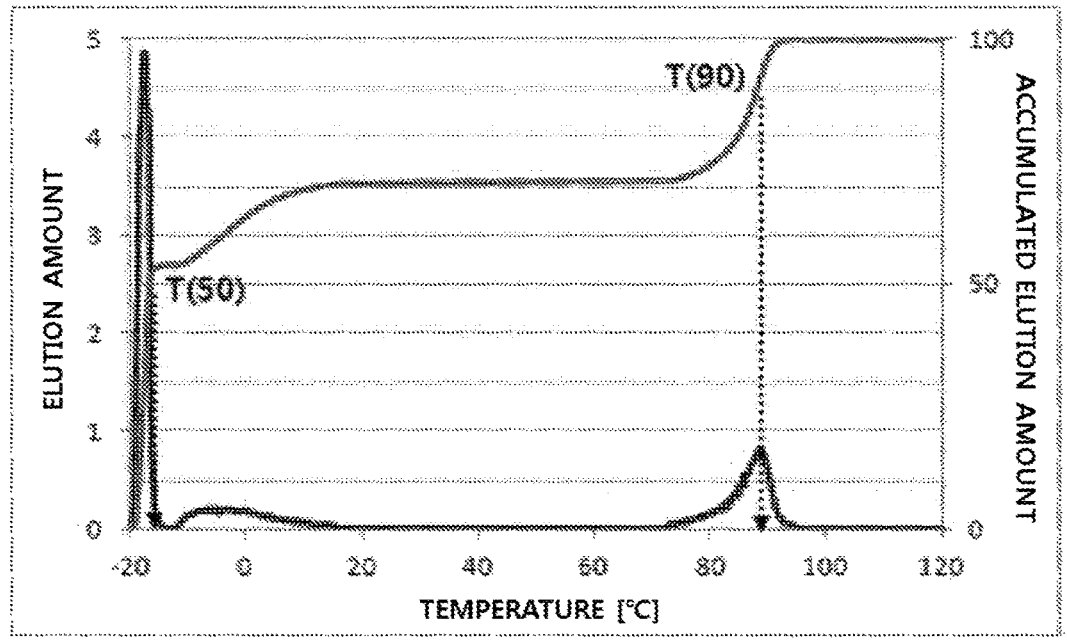
FIG. 6 illustrates a temperature rising elution fractionation (TREF) graph of an olefin-based polymer prepared in Preparation Example 6.
Figure 7:
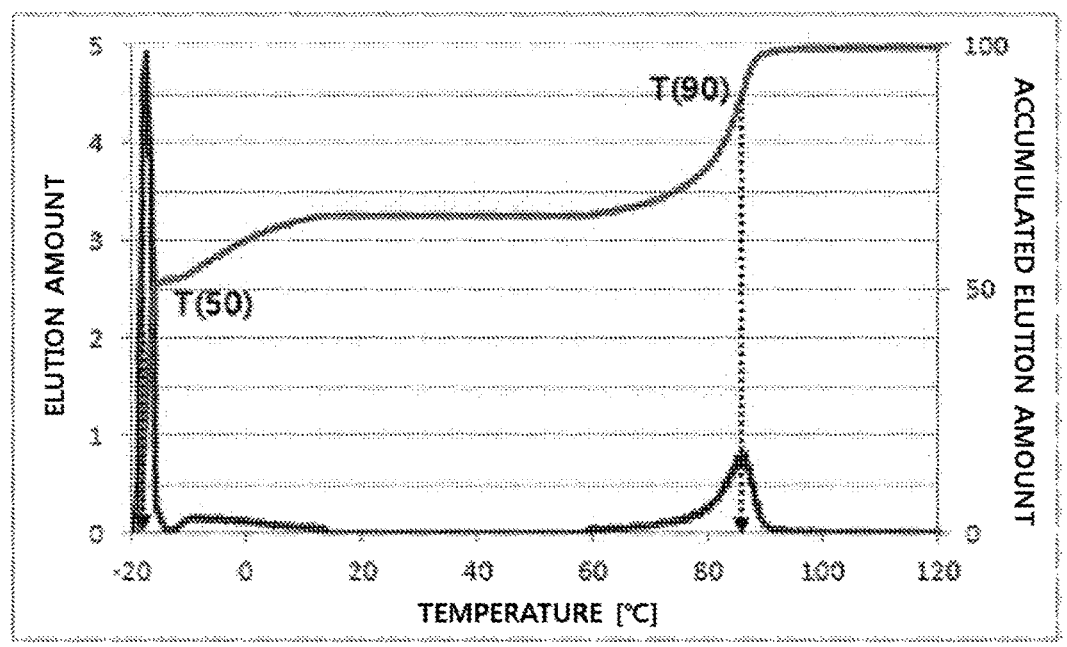
FIG. 7 illustrates a temperature rising elution fractionation (TREF) graph of an olefin-based polymer prepared in Preparation Example 7.
Figure 8:
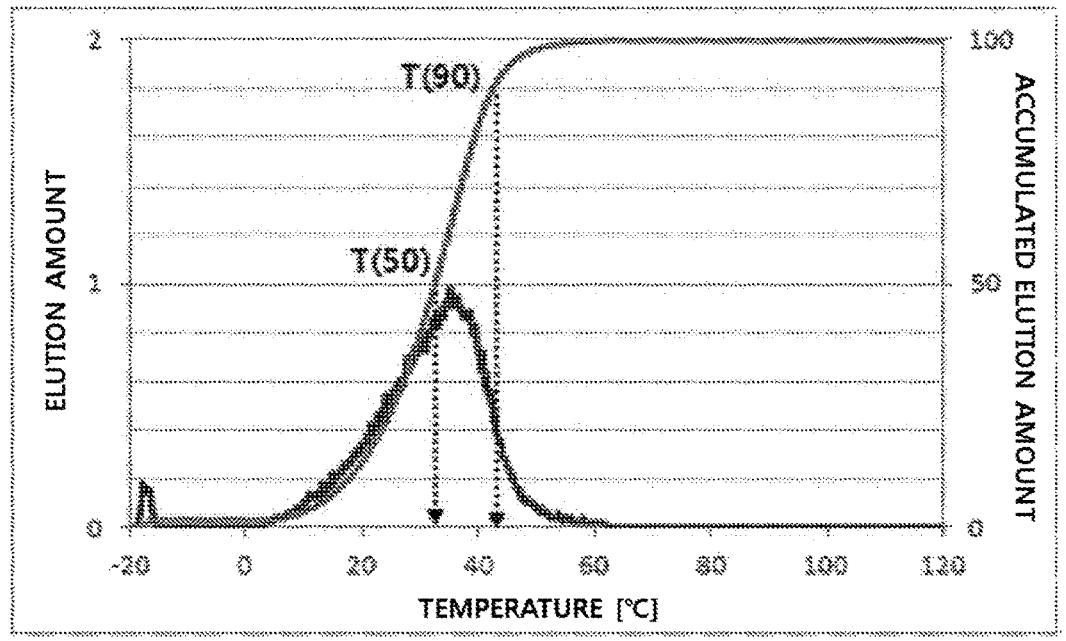
FIG. 8 illustrates a temperature rising elution fractionation (TREF) graph of an olefin-based polymer prepared in Comparative Example 1.
Figure 9:
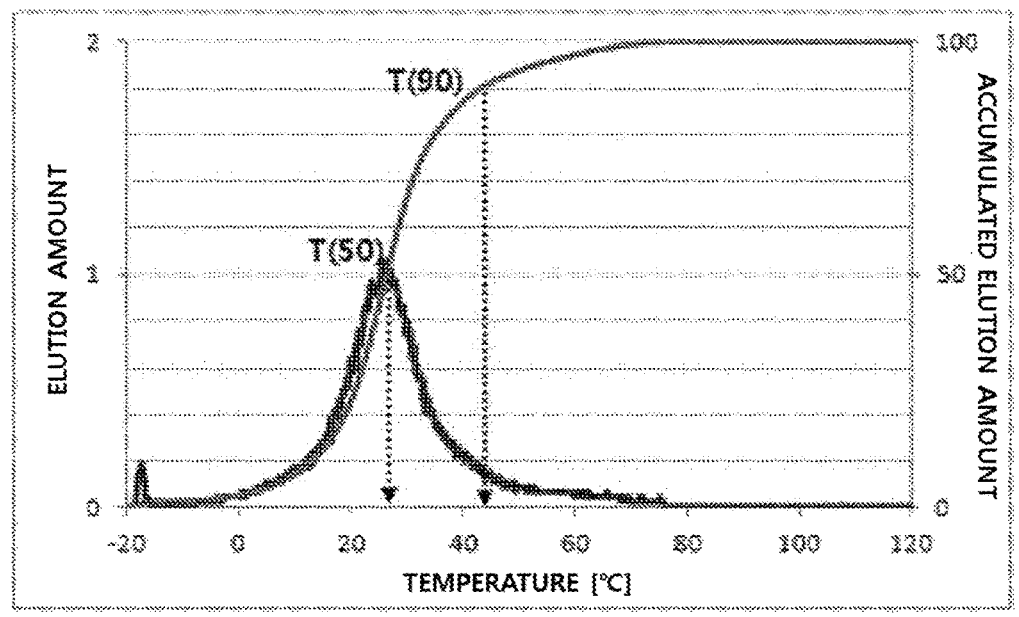
FIG. 9 illustrates a temperature rising elution fractionation (TREF) graph of an olefin-based polymer prepared in Comparative Example 2.
Figure 10:
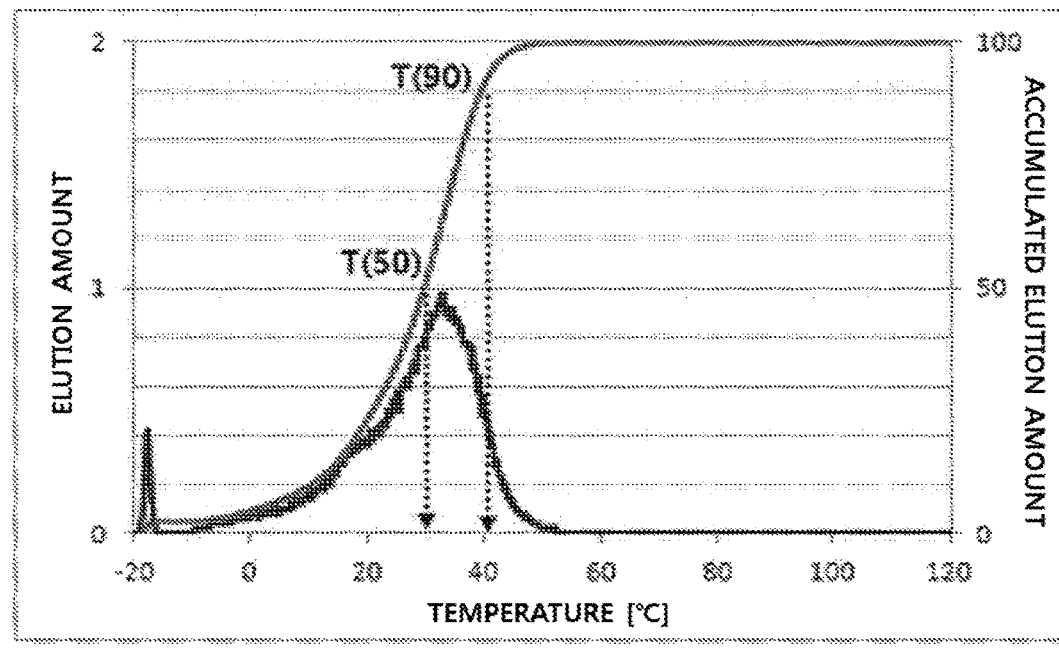
FIG. 10 illustrates a temperature rising elution fractionation (TREF) graph of an olefin-based polymer prepared in Comparative Example 3.
Figure 11:
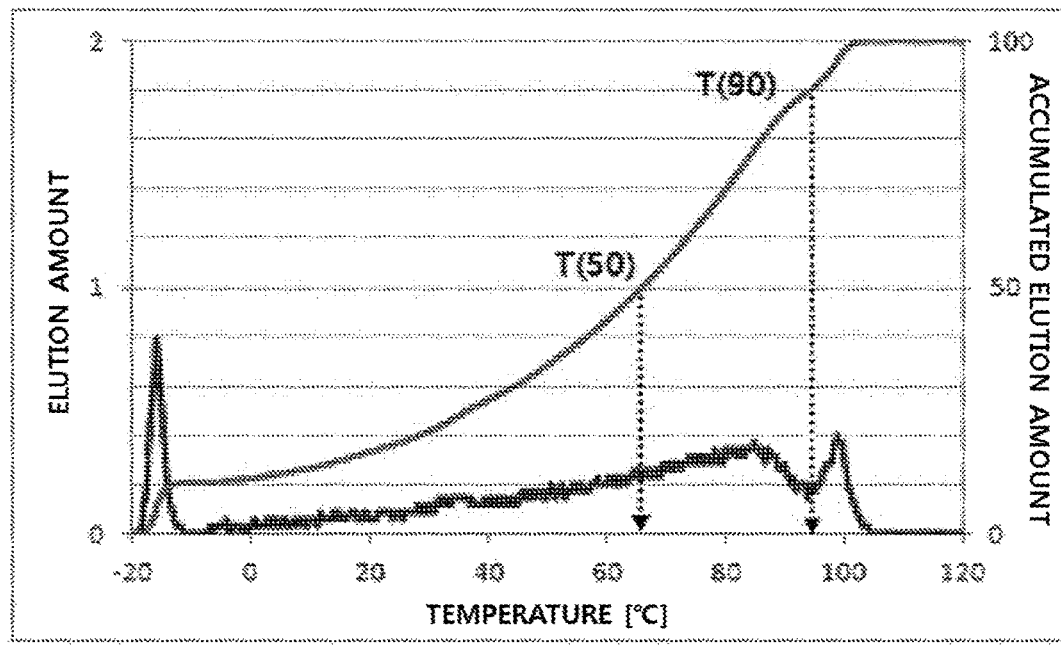
FIG. 11 illustrates a temperature rising elution fractionation (TREF) graph of an olefin-based polymer prepared in Comparative Example 4.
Figure 12:
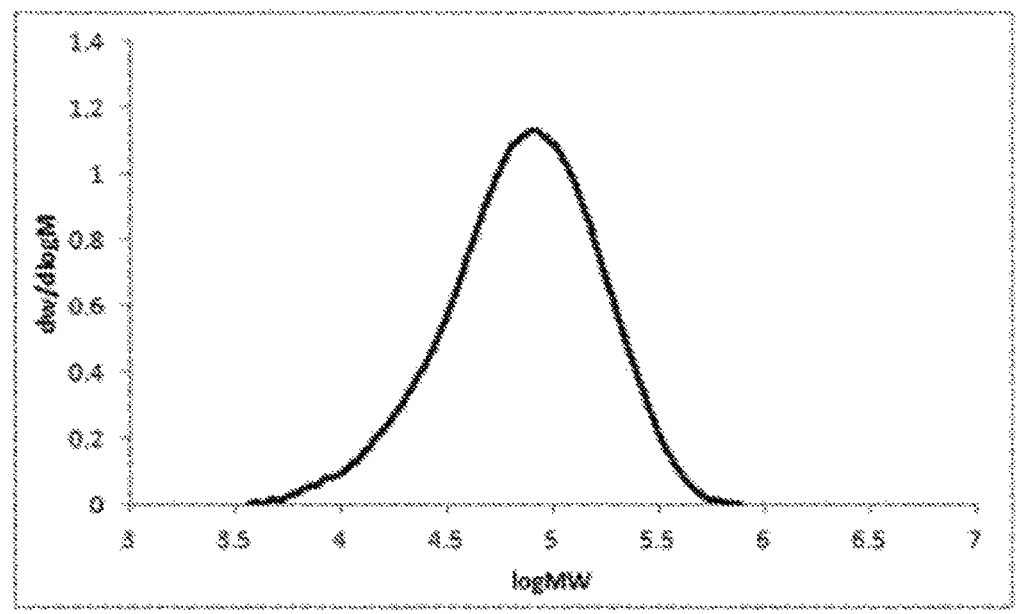
FIG. 12 illustrates a molecular weight distribution (GPC) graph of an olefin-based polymer prepared in Preparation Example 1.
Figure 13:
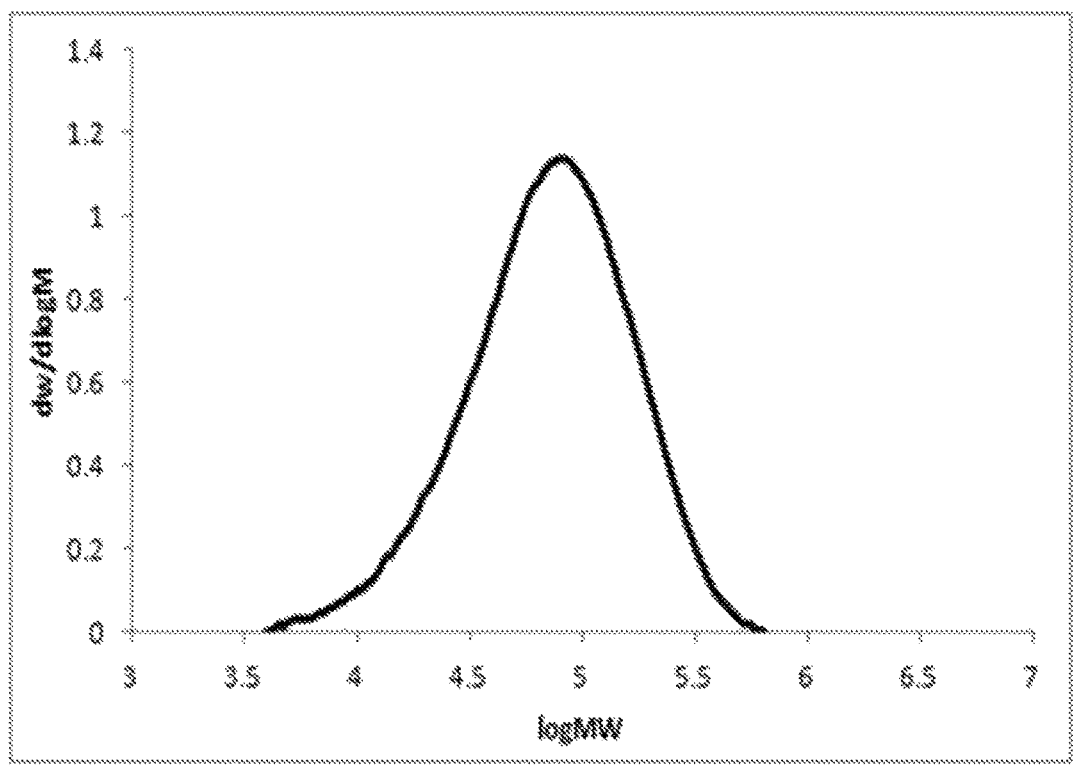
FIG. 13 illustrates a molecular weight distribution (GPC) graph of an olefin-based polymer prepared in Preparation Example 2
Figure 14:
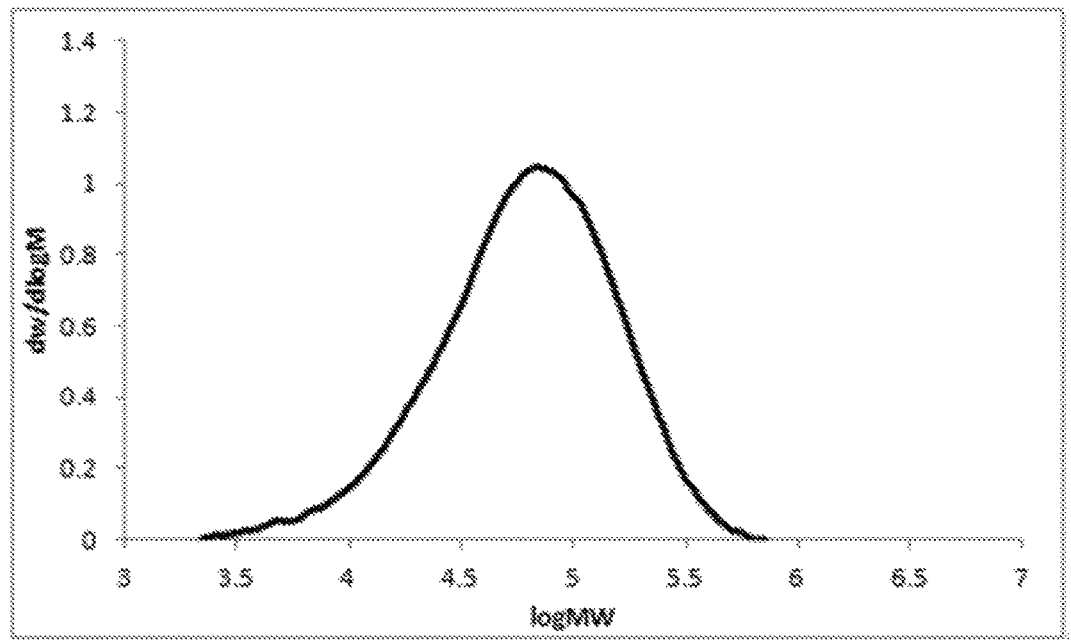
FIG. 14 illustrates a molecular weight distribution (GPC) graph of an olefin-based polymer prepared in Preparation Example 3.
Figure 15:
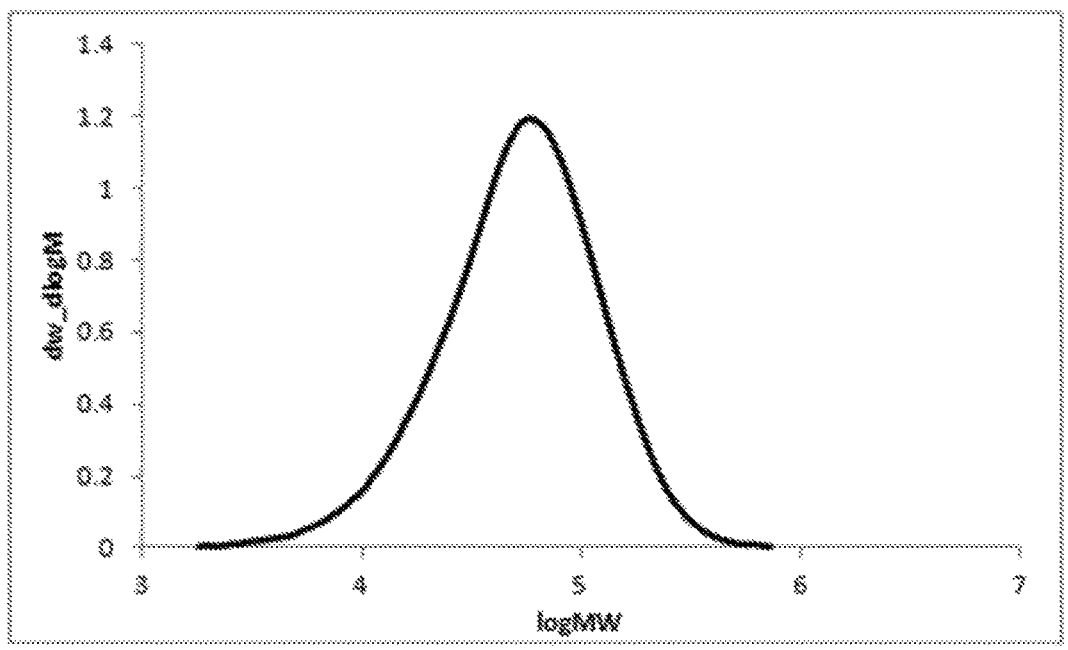
FIG. 15 illustrates a molecular weight distribution (GPC) graph of an olefin-based polymer prepared in Preparation Example 4.
Figure 16:
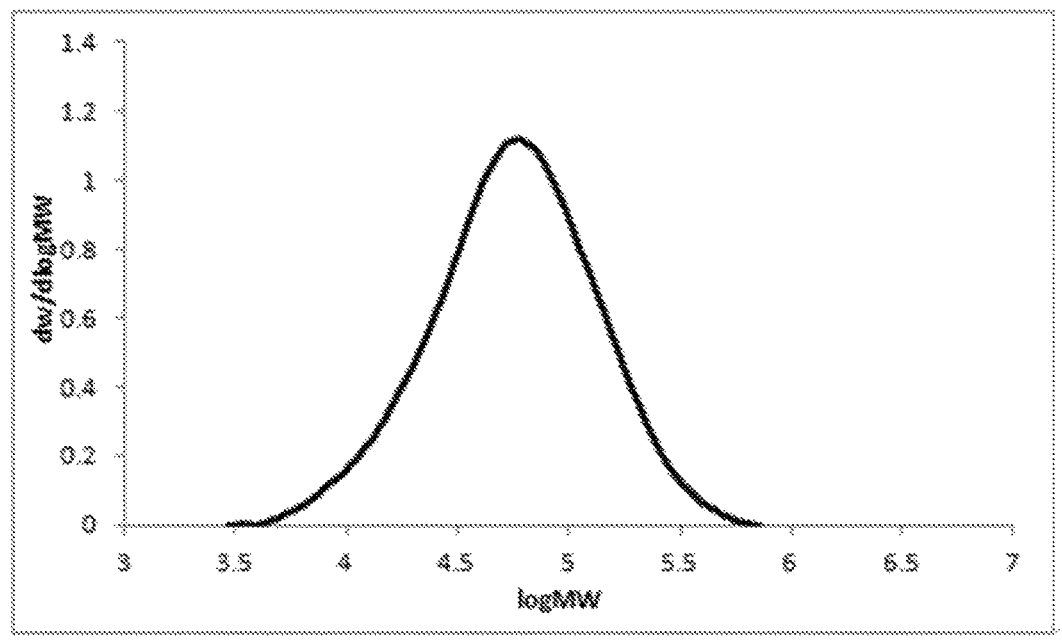
FIG. 16 illustrates a molecular weight distribution (GPC) graph of an olefin-based polymer prepared in Preparation Example 5.
Figure 17:
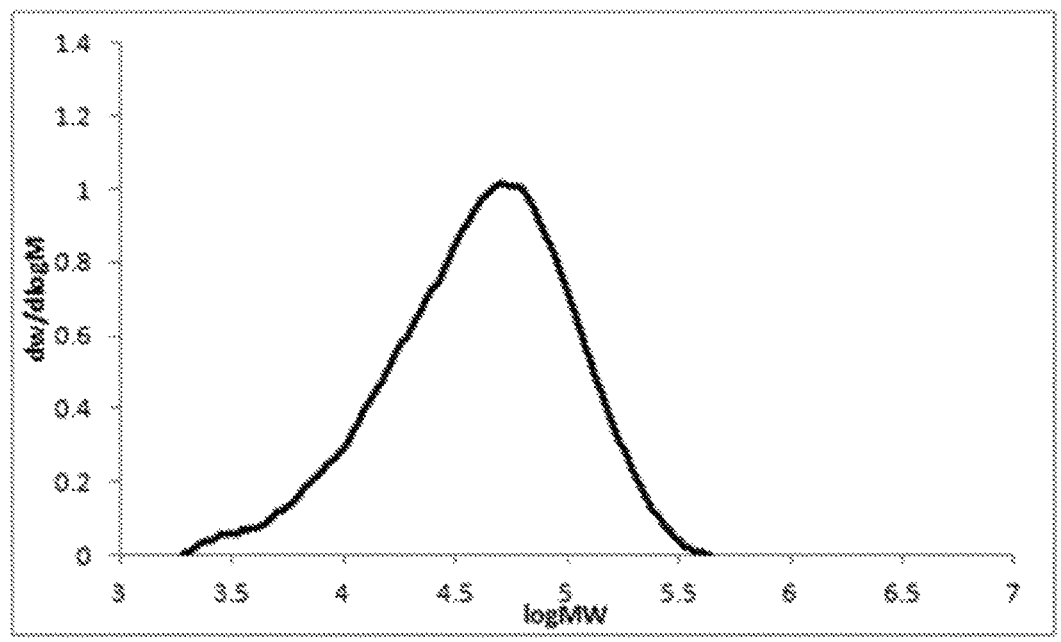
FIG. 17 illustrates a molecular weight distribution (GPC) graph of an olefin-based polymer prepared in Preparation Example 6.
Figure 18:
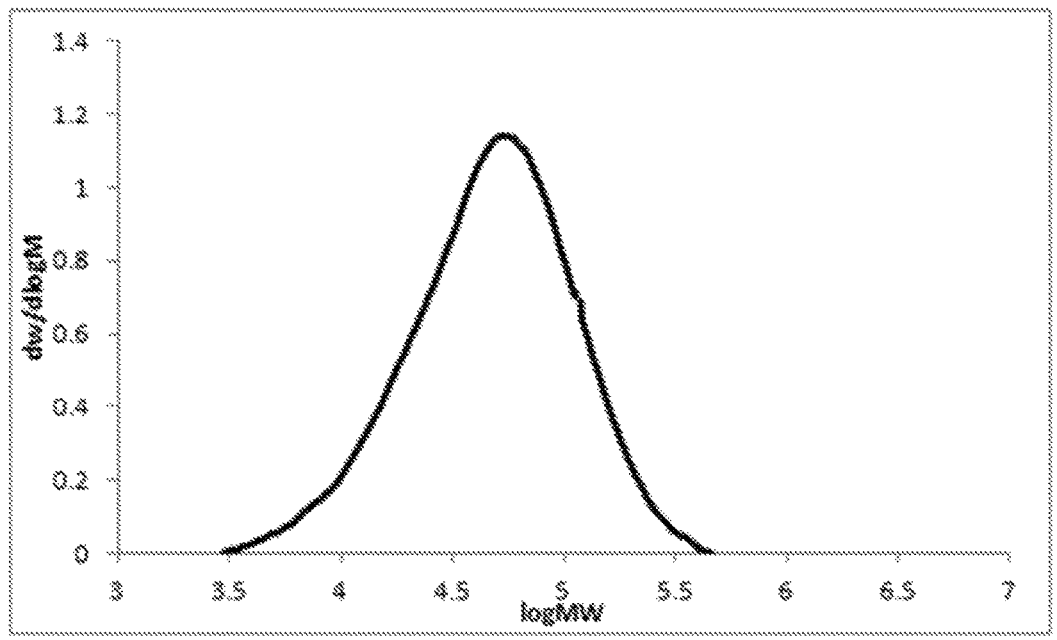
FIG. 18 illustrates a molecular weight distribution (GPC) graph of an olefin-based polymer prepared in Preparation Example 7.
Figure 19:
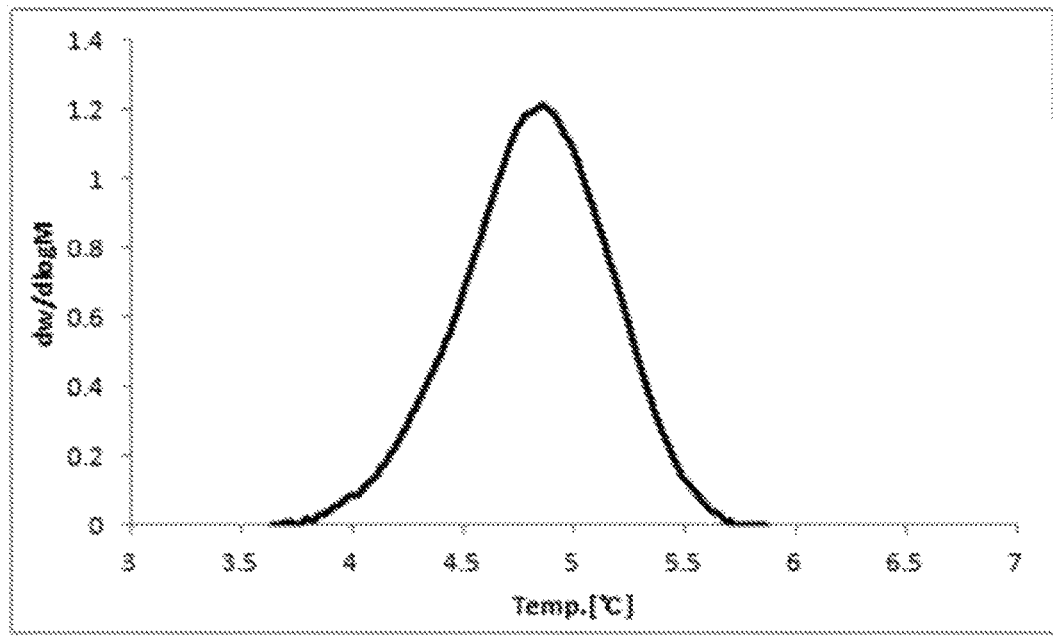
FIG. 19 illustrates a molecular weight distribution (GPC) graph of an olefin-based polymer prepared in Comparative Example 1.
Figure 20:
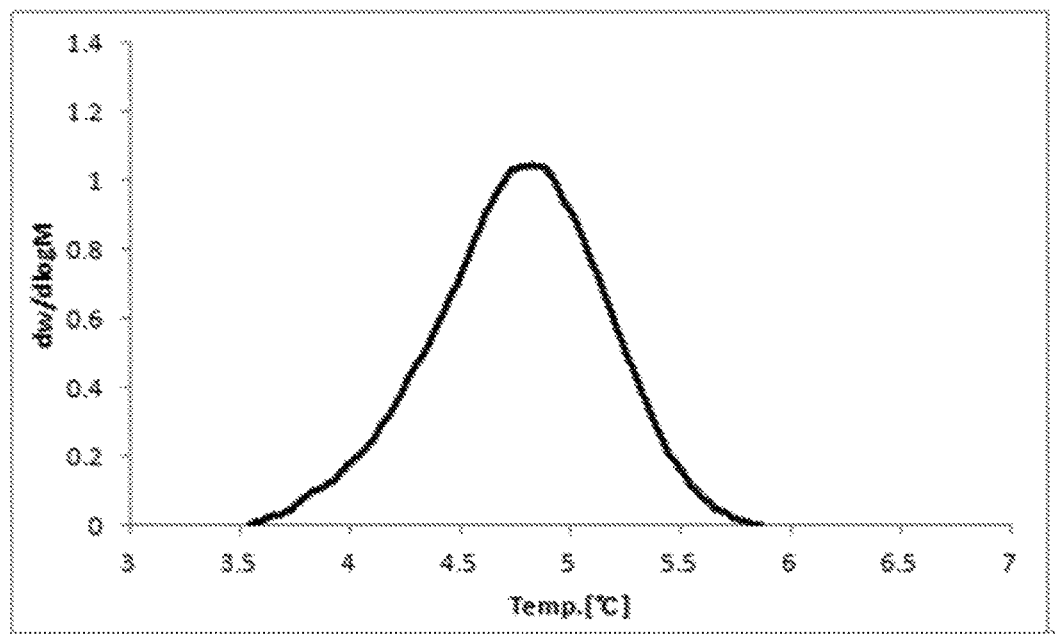
FIG. 20 illustrates a molecular weight distribution (GPC) graph of an olefin-based polymer prepared in Comparative Example 2.
Figure 21:
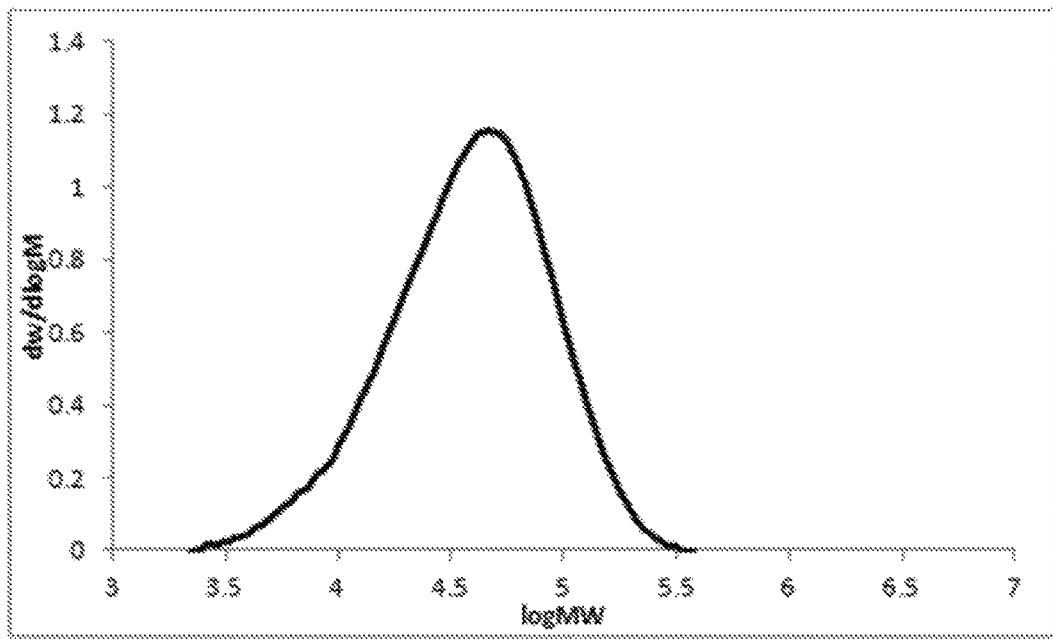
FIG. 21 illustrates a molecular weight distribution (GPC) graph of an olefin-based polymer prepared in Comparative Example 3.

The measured results are shown in FIGS. 1 to 21, and Table 1 below.

FIGS. 1 to 11 are temperature rising elution fractionation (TREF) graphs of the olefin-based polymers prepared in Preparation Examples 1-7 and Comparative Examples 1-4, and FIGS. 12 to 21 are molecular weight distribution (GPC) graphs of the olefin-based polymers prepared in Preparation Examples 1-7 and Comparative Examples 1-3.

accumulated elution amounts via purging and at 10° C. of 20 wt % or more, more particularly, 20-80 wt % based on the total amount of the olefin-based polymer, but the accumulated elution amounts of the olefin-based polymers of Comparative Examples 1 to 4 were significantly small and 15 wt % or less, more particularly, 3.3-13.3 weight.

EXPERIMENTAL EXAMPLE 2

Evaluation of Physical Properties of Polypropylene-based Composite Material

In order to verify the physical properties of compounds prepared in Examples 1, 2, and 6-8, and Comparative Examples 1 to 3, and 5, specimens were prepared by injection molding at a temperature of 200° C. using an injection machine, and the specimens thus prepared were stood in a room with a constant temperature and constant humidity for one day. Then, impact strength at a low temperature and at room temperature was measured. The physical properties of the specimens thus prepared are shown in Table 2 below.

TABLE 1

|  | Density (g/cc) | MI (g/10 min) | T(90) (° C.) | T(50) (° C.) | T(90) − T(50) (° C.) | Mw (g/mol) | MWD |
|---|---|---|---|---|---|---|---|
| Comparative Example 1 | 0.873 | 4.9 | 42.4 | 32.6 | 9.8 | 84935 | 1.78 |
| Comparative Example 2 | 0.869 | 5.1 | 43.2 | 26.4 | 16.8 | 80991 | 2.17 |
| Comparative Example 3 | 0.871 | 27.9 | 39.4 | 29.8 | 9.6 | 50460 | 1.94 |
| Comparative Example 4 | 0.914 | 4.4 | 94.4 | 66.0 | 28.4 | — | — |
| Preparation Example 1 | 0.873 | 4.6 | 90.8 | −0.4 | 91.2 | 95200 | 1.98 |
| Preparation Example 2 | 0.866 | 6.6 | 89.2 | −16.8 | 106 | 94123 | 1.97 |
| Preparation Example 3 | 0.863 | 6.8 | 87.0 | −8.8 | 95.8 | 86434 | 2.28 |
| Preparation Example 4 | 0.879 | 11.18 | 91.0 | 11.4 | 79.6 | 69434 | 1.95 |
| Preparation Example 5 | 0.874 | 4.1 | 91.4 | 17.8 | 73.6 | 76146 | 1.99 |
| Preparation Example 6 | 0.872 | 31.0 | 88.0 | −16.6 | 104.6 | 58387 | 2.39 |
| Preparation Example 7 | 0.870 | 33.1 | 86.0 | −16.2 | 102.2 | 64101 | 1.99 |

From the experimental results, the olefin-based polymers of Preparation Examples 1 to 7 according to the present invention showed a difference between T50 and T90 of 60° C. or more, but the olefin-based polymers of Comparative Examples 1 to 4 showed a value in a range of about 10° C. to 30° C.

In addition, the olefin-based polymers of Preparation Examples 1 to 7 according to the present invention showed two peaks of a peak (P1) and a peak (P2) on TREF in a density range of 0.855 g/cc to 0.910 g/cc. In contrast, the polymers of Comparative Examples 1 to 4 showed only one peak in the same density range.

In addition, the olefin-based polymers of Preparation Examples 1 to 7 according to the present invention showed a single peak on GPC and molecular weight distribution (MWD) of 1.5 to 2.5, which is narrow molecular weight distribution of the equivalent level as that of the polymers of Comparative Examples 1 to 3.

In addition, the olefin-based polymers of Preparation Examples 1 to 7 according to the present invention showed Maximum flexural stress and flexural modulus (Secant 1%): measured according to ASTM D790.

Maximum tensile strength: measured according to ASTM D638.

Impact strength at low temperature and at room temperature: measured according to ASTM D256, where the impact strength at room temperature was measured under room temperature (23° C.) conditions, and the impact strength at a low temperature was measured after standing in a chamber with a low temperature (−30° C.) for 12 hours or more.

TABLE 2

|  | Maximum flexural stress (kgf/cm$^2$) | Flexural modulus (Secant 1%) (kgf/cm$^2$) | Maximum tensile strength (kgf/cm$^2$) | Impact strength (−30° C.) (kgf · m/m) | Impact strength (23° C.) (kgf · m/m) |
|---|---|---|---|---|---|
| Comparative Example 1 | 242 | 8114 | 183 | 5.8 | 60.6 |

TABLE 2-continued

|  | Maximum flexural stress (kgf/cm²) | Flexural modulus (Secant 1%) (kgf/cm²) | Maximum tensile strength (kgf/cm²) | Impact strength (−30° C.) (kgf · m/m) | Impact strength (23° C.) (kgf · m/m) |
| --- | --- | --- | --- | --- | --- |
| Comparative Example 2 | 238 | 7943 | 180 | 5.5 | 60.8 |
| Comparative Example 3 | 257 | 8754 | 183 | 4.4 | 50.5 |
| Comparative Example 5 | 261 | 14205 | 161 | 4.3 | 49.0 |
| Example 1 | 245 | 8273 | 184 | 7.2 | 64.4 |
| Example 2 | 240 | 8321 | 179 | 8.0 | 64.0 |
| Example 6 | 244 | 8257 | 187 | 5.6 | 56.0 |
| Example 7 | 238 | 8225 | 180 | 6.1 | 42.7 |
| Example 8 | 242 | 14083 | 149 | 5.4 | 45.0 |

From the experimental results, the polypropylene-based composite materials of Examples 1, 2 and 6-8 according to the present invention showed the same degree of strength properties and even more improved results in view of impact strength at a low temperature when compared to those of Comparative Examples 1 to 3 and 5.

From the results, it may be found that the polypropylene-based composite material according to the present invention shows markedly improved impact strength, particularly, impact strength properties at a low temperature without using separate additive, and thus may be advantageous in the manufacture of products requiring excellent impact resistance.

The invention claimed is:

1. A polypropylene-based composite material comprising:
(A) polypropylene; and (B) an olefin-based polymer satisfying the following conditions of (b1) to (b4):
(b1) density: from 0.850 g/cc to 0.910 g/cc,
(b2) melt index (190° C., 2.16 kg load conditions): from 0.1 g/10 min to 100 g/10 min,
(b3) molecular weight distribution: from 1.5 to 3.0, and
(b4) i) two peaks are shown in a temperature range of −20° C. to 120° C. when taking measurements of temperature rising elution fractionation (TREF), and ii) a relation of T(90)−T(50)≥60° C. is satisfied, wherein T(90) is a temperature at which 90 wt % of the olefin-based polymer is eluted, and T(50) is a temperature at which 50 wt % of the olefin-based polymer is eluted.

2. The polypropylene-based composite material of claim 1, wherein the olefin-based polymer has two peaks in a temperature range of −20° C. to 120° C. when taking measurements of temperature rising elution fractionation, and a relation of T(90)≥70° C. is satisfied, where T(90) is a temperature at which 90 wt % of the olefin-based polymer is eluted.

3. The polypropylene-based composite material of claim 1, wherein an accumulated elution amount of the olefin-based polymer via purging of less than −20° C., or in a temperature range of −20° C. to 10° C. when taking measurements of temperature rising elution fractionation, is from 20 wt % to 80 wt % based on a total amount of the olefin-based polymer.

4. The polypropylene-based composite material of claim 1, wherein the olefin-based polymer has a weight average molecular weight of 10,000 g/mol to 500,000 g/mol.

5. The polypropylene-based composite material of claim 1, wherein the olefin-based polymer has a monomodal-type peak in a molecular weight distribution curve when taking measurements of gel permeation chromatography.

6. The polypropylene-based composite material of claim 1, wherein the olefin-based polymer is a copolymer of an ethylene monomer and an alpha-olefin comonomer.

7. The polypropylene-based composite material of claim 1, wherein the olefin-based polymer is prepared by using a continuous solution polymerization reaction in the presence of a metallocene-based catalyst composition comprising at least one kind of a transition metal compound, and wherein the olefin-based polymer comprises no block formed by linearly connecting at least two repeating units which are derived from one monomer among monomers composing the olefin-based polymer.

8. The polypropylene-based composite material of claim 1, wherein the olefin-based polymer is a random copolymer.

9. The polypropylene-based composite material of claim 1, wherein the polypropylene has a melt index of 0.5 g/10 min to 100 g/10 min when taking measurements at 230° C. and 2.16 kg load.

10. The polypropylene-based composite material of claim 1, wherein the polypropylene is an impact copolymer having a melt index of 0.5 g/10 min to 100 g/10 min when taking measurements at 230° C. and 2.16 kg load.

11. The polypropylene-based composite material of claim 1, wherein the polypropylene-based composite material comprises the polypropylene and the olefin-based polymer in an weight ratio of 50:50 to 90:10.

12. The polypropylene-based composite material of claim 1, wherein the polypropylene-based composite material further comprises an inorganic filler.

13. The polypropylene-based composite material of claim 12, wherein the polypropylene-based composite material comprises the inorganic filler in an amount of 0.1 parts by weight to 40 parts by weight based on 100 parts by weight of the polypropylene, and the inorganic filler has an average diameter ($D_{50}$) of 1 µm to 20 µm.

14. A polypropylene-based composite material comprising:
(A2) from 75 wt % to 97 wt % of at least one random propylene copolymer having a melting point when taking measurements of differential scanning calorimetry in a range of 120° C. to 160° C., and a melt flow rate in a range of 5 g/10 min to 120 g/10 min; and
(B2) from 3 wt % to 25 wt % of an ethylene α-olefin copolymer satisfying the following conditions of (b21) to (b25):
(b21) density: from 0.860 g/cc to 0.910 g/cc,
(b22) melt index (190° C., 2.16 kg load conditions): from 0.1 g/10 min to 200 g/10 min,
(b23) molecular weight distribution: from 1.5 to 3.0,
(b24) i) two peaks are shown in a temperature range of −20° C. to 120° C. when taking measurements of temperature rising elution fractionation, and ii) a relation of T(90)−T(50)≥60° C. is satisfied, wherein T(90) is a temperature at which 90 wt % of the olefin-based polymer is eluted, and T(50) is a temperature at which 50 wt % of the olefin-based polymer is eluted, and
(b25) weight average molecular weight: from 10,000 g/mol to 500,000 g/mol.

15. The polypropylene-based composite material of claim 14, wherein the ethylene α-olefin copolymer is an ethylene/octene elastomer.

16. The polypropylene-based composite material of claim 14, wherein the polypropylene-based composite material further comprises from 5 wt % to 15 wt % of at least one propylene α-olefin hybrid polymer based on a total amount of the polypropylene-based composite material, the propylene α-olefin hybrid polymer having a melting point when taking measurements of differential scanning calorimetry in a range of less than 110° C., a fusion heat in a range of less than 50 J/g, crystallinity in a range of 1 wt % to 40 wt %, and a melting flow rate in a range of less than 80 g/10 min.

17. A molded article manufactured using the polypropylene-based composite material according to claim 1.

18. A automobile part manufactured using the polypropylene-based composite material according to claim 1.

* * * * *